US008058275B2

(12) United States Patent
Xu et al.

(10) Patent No.: US 8,058,275 B2
(45) Date of Patent: *Nov. 15, 2011

(54) DIAZABENZO[DE] ANTHRACEN-3-ONE COMPOUNDS AND METHODS FOR INHIBITING PARP

(75) Inventors: Weizheng Xu, Ellicott City, MD (US); Greg Delahanty, Nottingham, MD (US); Jie Zhang, Ellicott City, MD (US)

(73) Assignee: Eisai Inc., Woodcliff, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/910,448

(22) Filed: Oct. 22, 2010

(65) Prior Publication Data

US 2011/0092478 A1    Apr. 21, 2011

Related U.S. Application Data

(63) Continuation of application No. 11/814,238, filed as application No. PCT/US06/01729 on Jan. 19, 2006, now Pat. No. 7,820,668.

(60) Provisional application No. 60/712,140, filed on Aug. 30, 2005, provisional application No. 60/644,584, filed on Jan. 19, 2005.

(51) Int. Cl.
*C07D 487/06* (2006.01)
*A61K 31/5025* (2006.01)
(52) U.S. Cl. ................ 514/250; 544/235; 544/248
(58) Field of Classification Search .............. 514/250; 544/235, 248
See application file for complete search history.

(56) References Cited

U.S. PATENT DOCUMENTS

| 6,291,425 | B1 | 9/2001 | Li et al. |
| 6,348,475 | B1 | 2/2002 | Zhang et al. |
| 6,716,828 | B1 | 4/2004 | Li et al. |
| 7,307,080 | B2 | 12/2007 | Li et al. |
| 7,456,178 | B2 | 11/2008 | Kalish et al. |
| 7,601,719 | B2 | 10/2009 | Kalish et al. |
| 7,820,668 | B2 * | 10/2010 | Xu et al. ............ 514/250 |

FOREIGN PATENT DOCUMENTS

| WO | WO-01/16137 A1 | 3/2001 |
| WO | WO-2004/105700 A2 | 12/2004 |

OTHER PUBLICATIONS

Gagne et al. Current Opinion in Cell Biology 2006, 18:145-151.*
Chalmers (TiPS vol. 17, pp. 166-172 Apr. 1996).*
Chalmers, TIPS, vol. 17, 166-172 (Apr. 1996) Gagne et al.,.
Current Opinion in Cell Biology, 18, 145-151 (2006) Combs et al.,.
Journal of Heterocyclic Chemistry, vol. 26, 1885-1886 (1989) E.S. Newlands et al.,.
"Temozolomide: A Review of its Discovery, Chemical Properties, Pre-clinical Development and Clinical Trails" Cancer Treatment Review, 23, 35-61 (1997).

* cited by examiner

*Primary Examiner* — Kahsay T Habte
(74) *Attorney, Agent, or Firm* — Lathrop & Gage LLP; Brian C. Trinque

(57) ABSTRACT

The present invention relates to diazabenzo[de]anthracen-3-one compounds which inhibit poly(ADP-ribose) polymerase ("PARP"), compositions containing these compounds and methods for using these PARP inhibitors to treat, prevent and/or ameliorate the effects of the conditions described herein.

31 Claims, 2 Drawing Sheets

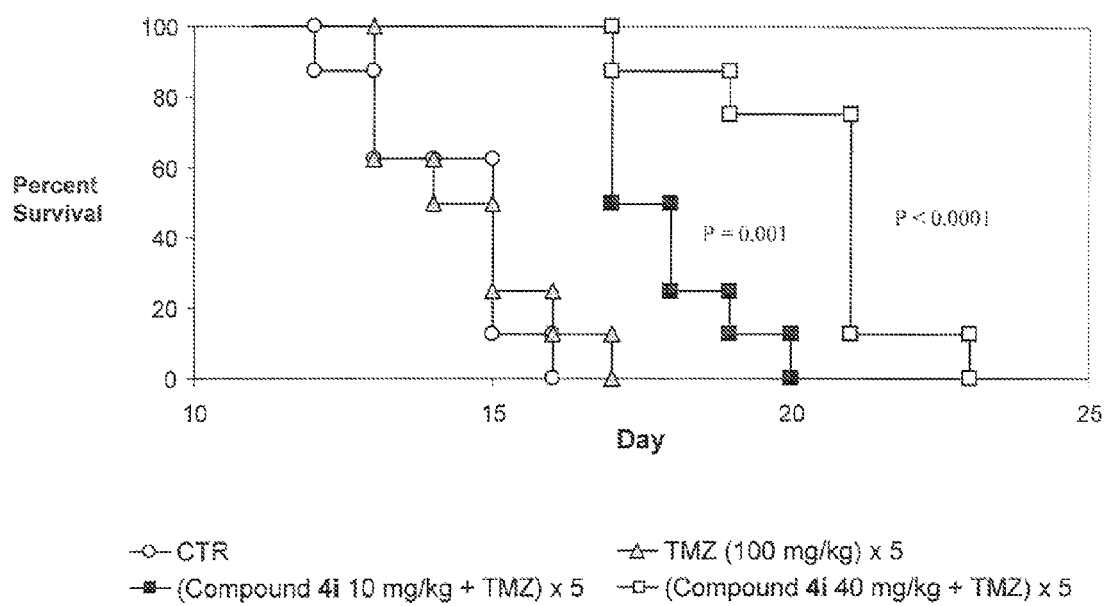

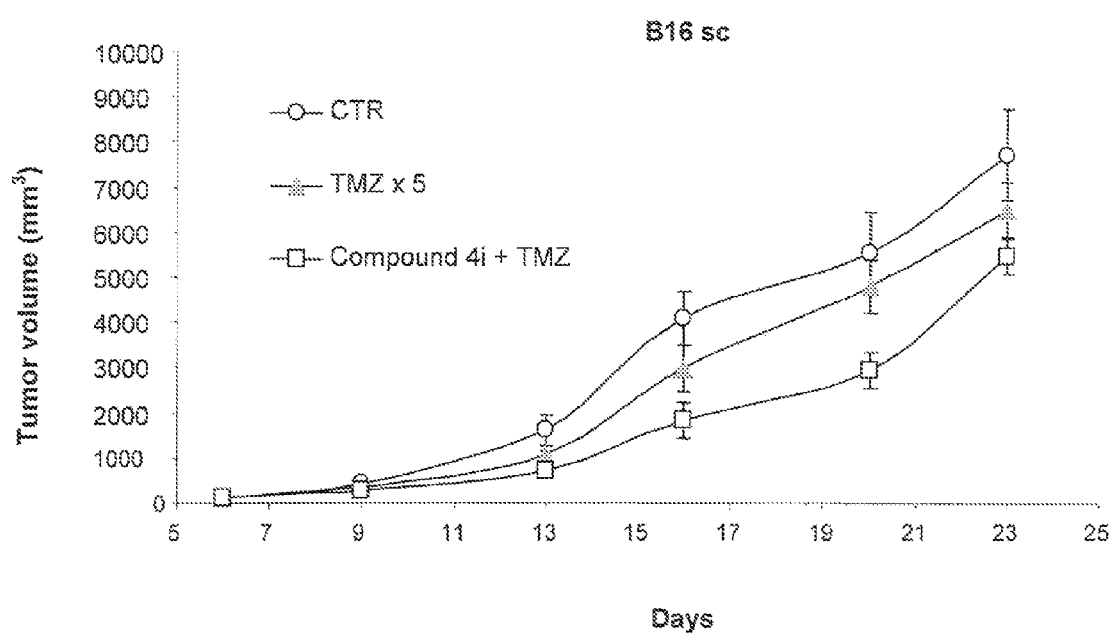
Fig. II. Efficacy of Compound 4i + TMZ against B16 melanoma growing s.c. in B6D2F1 mice

DIAZABENZO[DE] ANTHRACEN-3-ONE COMPOUNDS AND METHODS FOR INHIBITING PARP

CROSS-REFERENCE TO RELATED APPLICATIONS

The present application is a continuation application of U.S. application Ser. No. 11/814,238, filed on Mar. 21, 2008 now U.S. Pat. No. 7,820,668. U.S. application Ser. No. 11/814,238 is a national stage of PCT/US06/01729, filed on Jan. 19, 2006, which claims the benefit of U.S. application 60/644,584, filed on Jan. 19, 2005 and U.S. application 60/712,140, filed Aug. 30, 2005. The entire contents of these applications are fully incorporated herein by reference.

FIELD OF THE INVENTION

The present invention relates to diazabenzo[de]anthracen-3-one compounds which inhibit poly(ADP-ribose) polymerase ("PARP"), compositions containing these compounds and methods for using these PARP inhibitors to treat, prevent and/or ameliorate the effects of the conditions described herein.

BACKGROUND

PARP (EC 2.4.2.30), also known as PARS (for poly(ADP-ribose) synthetase), or ADPRT (for NAD:protein (ADP-ribosyl) transferase (polymerising)) is a major nuclear protein of 116 kDa. It is mainly present in almost all eukaryotes. The enzyme synthesizes poly(ADP-ribose), a branched polymer that can consist of over 200 ADP-ribose units from NAD. The protein acceptors of poly(ADP-ribose) are directly or indirectly involved in maintaining DNA integrity. They include histones, topoisomerases, DNA and RNA polymerases. DNA ligases, and $Ca^{2+}$- and $Mg^+$-dependent endonucleases.

PARP protein is expressed at a high level in many tissues, most notably in the immune system, heart, brain and germline cells. Under normal physiological conditions, there is minimal PARP activity. However, DNA damage causes an immediate activation of PARP by up to 500-fold. Among the many functions attributed to PARP is its major role in facilitating DNA repair by ADP-ribosylation and therefore coordinating a number of DNA repair proteins. As to result of PARP activation, NAD levels significantly decline. While many endogenous and exogenous agents have been shown to damage DNA and activate PARP, peroxynitrite, formed from a combination of nitric oxide (NO) and superoxide, appears to be a main perpetrator responsible for various reported disease conditions in vivo, e.g., during shock, stroke and inflammation.

It is also known that PARP inhibitors, such as 3-amino benzamide, affect DNA repair generally in response, for example, to hydrogen peroxide or gamma-radiation. Cristovao et al., "Effect of a Poly(ADP-Ribose) Polymerase inhibitor on DNA Breakage and Cytotoxicity induced by Hydrogen Peroxide and γ-Radiation." Terato., Carcino., and Muta., 16:219-27 (1996). Specifically, Cristovao et al. observed a PARP-dependent recovery of DNA strand breaks in leukocytes treated with hydrogen peroxide.

The nuclear enzyme poly(ADP-ribose) polymerase-1 (PARP-1) plays a key role in facilitating base excision repair and other cellular processes, it has been proposed that PARP-1 acts as a molecular DNA nick sensor, detecting DNA single-strand breaks and recruiting the appropriate repair enzymes. PARP-1 hinds to DNA strand breaks via two zinc fingers in the amino-terminal DNA binding domain of the enzyme, its activity being dependent on DNA binding, The enzyme acts as a homodimer catalyzing the transfer of ADP-ribose from the substrate NAD+ to acceptor proteins, including PARP-1 itself. Extensive negatively charged polymers of PAR are thereby formed, causing electrostatic repulsion of DNA strands and chromatin proteins, the latter allowing base excision repair complexes access to the damaged strand and subsequent DNA repair, After initial activation by a strand break, PARP-1 is released from the DNA, the polymer degraded by PAR glycohydrolase, and the PARP-1 enzyme is then available for a further round of DNA binding and activation. Plummer, et al., 11(9) Clin. Cancer Res. 3402 (2005).

PARP inhibitors have been reported to be effective, as synergists or potentiators, in radiosensitizing hypoxic tumor cells. PARP inhibitors have also been reported to be effective as synergists in preventing tumor cells from recovering from potentially lethal damage of DNA after radiation therapy, presumably by their ability to prevent DNA repair, U.S. Pat. Nos. 5,032,617; 5,215,738; and 5,041,653.

There is considerable interest in the development of PARP inhibitors as both chemopotentiators and radiopotentiators for use in cancer therapy and to limit cellular damage after ischemia or endotoxic stress. In particular, potentiation of temozolomide cytotoxicity observed in preclinical studies with potent PARP-1 inhibitors reflects inhibition of base excision repair and subsequent cytotoxicity due to Incomplete processing of $N^7$-methylguanine and $N^3$-methyladenine. There is now a body of preclinical data demonstrating that the cytotoxicity of temozolomide is potentiated by coadministration of a PARP inhibitor either in vitro or in vivo. Plummer, et al., Clin. Cancer Res., 11(9), 3402 (2005).

Temozolomide, a DNA methylating agent, induces DNA damage, which is repotted by $O^6$-alkylguanine alkyltransferase (ATase) and poly(ADP-ribose) polymerase-1 (PARP-1)-dependent base excision repair. Temozolomide is an orally available monofunctional DNA alkylating agent used to treat gliomas and malignant melanoma. Temozolomide is rapidly absorbed and undergoes spontaneous breakdown to form the active monomethyl triazene, 5-(3-methyl-1-triazeno)imidazole-4-carboxamide. Monomethyl triazene forms several DNA methylation products, the predominate species being $N^7$-methylguanine (70%), $N^3$-methyladenine (9%), and $O^6$-methylguanine (5%). Unless repaired by $O^6$-alkylguanine alkyltransferase, $O^6$-methylguanine is cytotoxic due to mispairing with thymine during DNA replication. This mispairing is recognized on the daughter strand by mismatch repair proteins and the thymine excised. However, unless the original $O^6$-methylguanine nucleotide in the parent strand is repaired by ATase-mediated removal of the methyl adduct can be reinserted. Repetitive futile rounds of thymine excision and incorporation opposite an unrepaired $O^6$-methylguanine nucleotide causes a state of persistent strand breakage and the MutS branch of mismatch repair system signals G2-M cell cycle arrest and the initiation of apoptosis. The quantitatively more important $N^7$-methylguanine and $N^3$-methyladenine nucleotide alkylation products formed by temozolomide are rapidly repaired by base excision repair. Plummer, et al., Clin. Cancer Res., 11(9), 3402 (2005).

Chemosensitization by PARP inhibitors is not limited to temozolomide. Cytotoxic drugs, generally, or radiation can induce activation of PARP-1, and it has been demonstrated that inhibitors of PARP-1 can potentiate the DNA damaging and cytotoxic effects of chemotherapy and irradiation. Kock, et al., 45 J. Med. Chem. 4961 (2002), PARP-1 mediated DNA repair in response to DNA damaging agents represents a mechanism for drug resistance in tumors, and inhibition of this enzyme has been shown to enhance the activity of ionizing radiation and several cytotoxic antitumor agents, including temozolomide and topotecan. Suto of al., in U.S. Pat. No. 5,177,075, disclose several isoquinolines used for enhancing the lethal effects of ionizing radiation or chemotherapeutic agents on tumor cells. Weltin et al., "Effect of 6(5H)-Phenanthridinone, an inhibitor of Poly(ADP-ribose) Polymerase, on Cultured Tumor Cells", *Oncol. Res.*, 6:9, 399-403 (1994) disclose the inhibition of PARP activity, reduced proliferation of tumor cells, and a marked synergistic effect when tumor cells are co-treated with an alkylating drug. PARP-1 is thus a potentially important therapeutic target for enhancing DNA-damaging cancer therapies.

Large numbers of known PARP inhibitors have been described in Banasik et al., "Specific Inhibitors of Poly(ADP-Ribose) Synthetase and Mono(ADP-Ribosyl)-Transferase", *J. Biol. Chem.*, 267:3, 1569-75 (1992), and in Banasik et al., "Inhibitors and Activators of ADP-Ribosylation Reactions", *Molec. Cell. Biochem.*, 138, 185-97 (1994), However, effective use of these PARP inhibitors, in the ways discussed above, has been hunted by the concurrent production of unwanted side-effects, See Milam et al., "Inhibitors of Poly (Adenosine Diphosphate-Ribose) Synthesis; Effect on Other Metabolic Processes," *Science*. 223, 589-91 (1984).

In addition to the above, PARP inhibitors have been disclosed and described in the following international patent applications: WO 00/42040; WO 00/39070; WO 00/39104; WO 99/11623; WO 99/1162.8; WO 99/11622; WO 99/59975; WO 99/11644; WO 99/11945; WO 99/11649; and WO 99/59973. A comprehensive review of the state of the art has been published by Li and Zhang in IDrugs 2001, 4(7); 804-812 (PharmaPress Ltd ISSN 1369-7056).

The ability of PARP-inhibitors to potentiate the lethality of cytotoxic agents, whether by radiosensitizing tumor cells to ionizing radiation, or by chemosensitizing tumor cells to the cytotoxic effects of chemotherapeutic agents has been reported in, inter alia, US 2002/0028815; US 2003/0134843; US 2004/0067949; White A W, et al., 14 Bioorg. & Med. Chem Letts. 2433 (2(104); Canon Koch S S, et al., 45 J. Med. Chem. 4961 (2002); Skalitsky al, et al., 46 J. Med. Chem. 210 (2003); Farmer H, at 434 Nature 917 (14 Apr. 2005); Plummer E R, et al, 11(9) Clin. Cancer Res. 3402 (2005); Tikhe J G, et al, 47 J. Med., Chem. 5467 (2004); Griffin R. J., et al., WO 98/33802; and Helleday T, et al., WO 2005/012305.

The induction of peripheral neuropathy is a common factor in limiting therapy with chemotherapeutic drugs. Quasthoff and Hartung, *J. Neurology,* 249, 9-17 (2002). Chemotherapy induced neuropathy is a side-effect encountered following the use of many of the conventional (e.g. Taxol, vincritine, cisplatin) and newer chemotherapies (eg velcade, epothilone). Depending on the substance used, a pure sensory and painful neuropathy (with cisplatin, oxaliplatin, carboplatin) or a mixed sensorimotor neuropathy with or without involvement of the autonomic nervous system (with vincristine, taxol, suramin) can ensue. Neurotoxicity depends on the total cumulative dose and the type of drug used. In individual cases neuropathy can evolve even after a single drug application. The recovery from symptoms is often incomplete and a bona period of regeneration is required to restore function. Up to now, no drug is available to reliably prevent or cure chemotherapy-induced neuropathy.

There continues to be a need for effective and potent PARP inhibitors Which enhance the lethal effects of ionizing radiation and/or chemotherapeutic agents on tumor cells while producing minimal sine-effects.

SUMMARY OF THE INVENTION

The present invention provides diazabenzo[de]anthracen-3-one compounds which inhibit poly(ADP-ribose) polymerase ("PARP"), compositions containing these compounds and methods for using these PARP inhibitors to treat, prevent and/or ameliorate the effects of the conditions described herein.

The present invention also provides a diazabenzo[de]anthracen-3-one compound selected from the following Group I compounds:

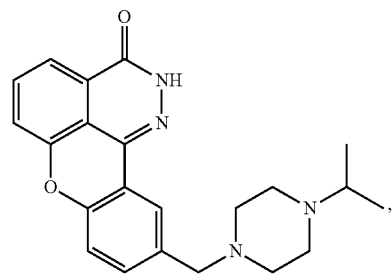

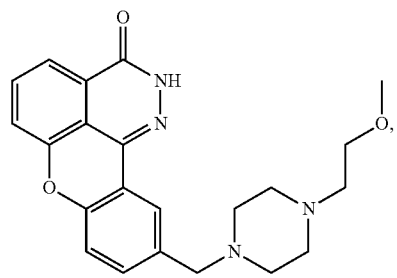

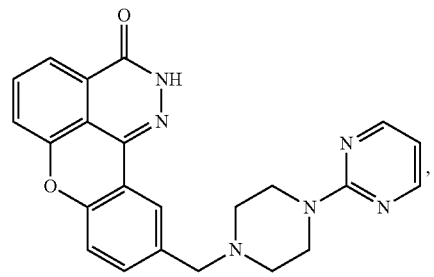

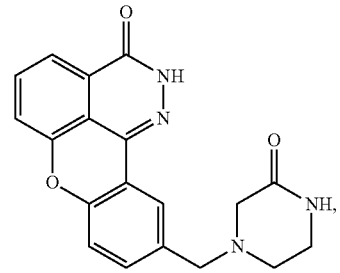

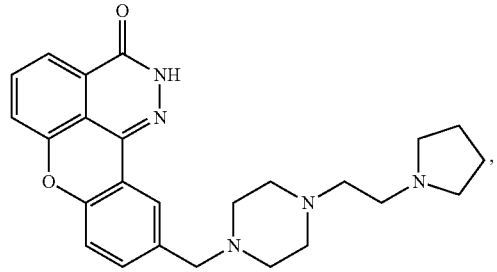

5
-continued
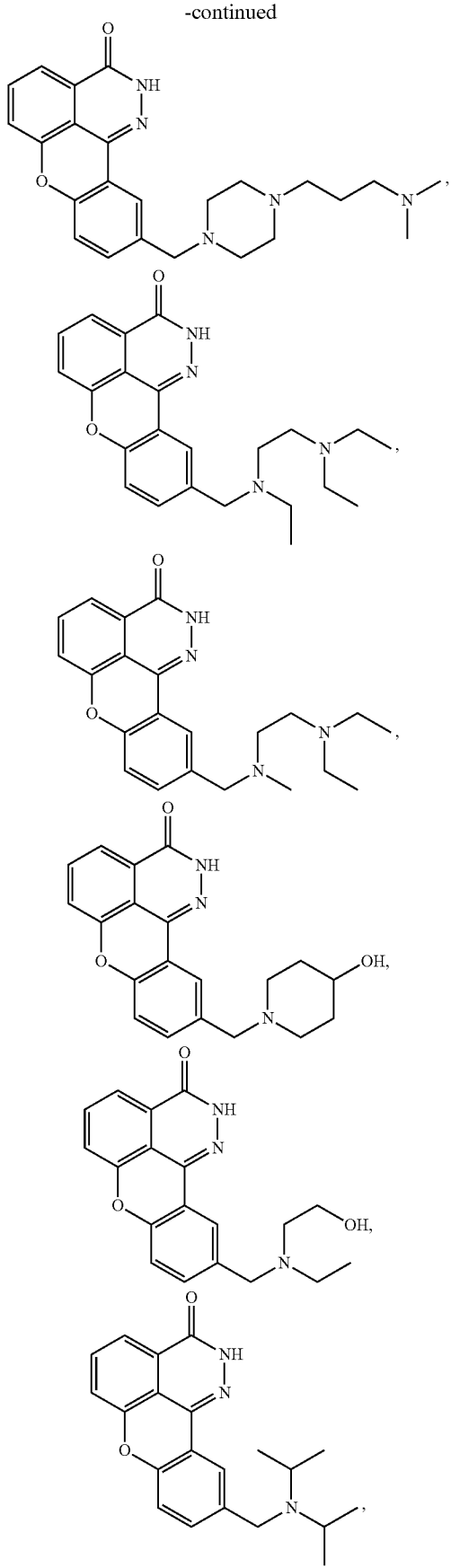
6
-continued
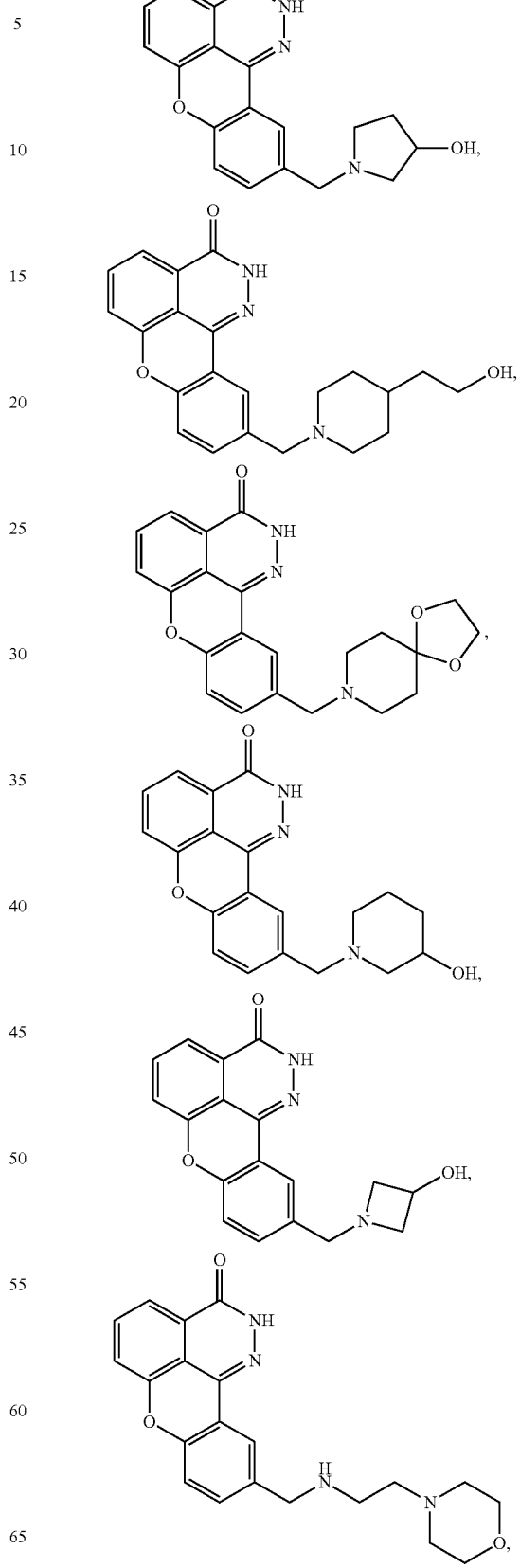

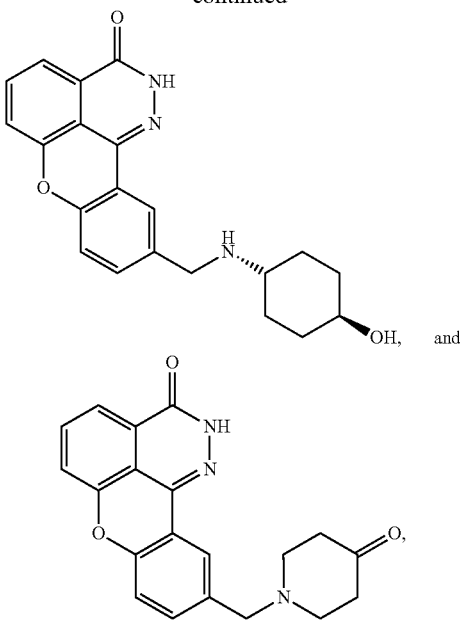

and pharmaceutically acceptable salts, hydrates, esters, solvates, and mixtures thereof.

The present Invention also relates to a pharmaceutical composition comprising (i) a therapeutically effective amount of a compound of Group I and (ii) pharmaceutically acceptable carrier.

The present invention provides compounds which Inhibit the in vitro and/or in vivo polymerase activity of poly(ADP-ribose) polymerase (PARP), and compositions containing the disclosed compounds.

The present invention provides methods to inhibit, limit and/or control the an/or in vivo polymerase activity of poly (ADP-ribose) polymerase (PARP) in solutions, cells, tissues, organs or organ systems. In one embodiment, the present invention provides methods of limiting or inhibiting PARP activity in a mammal, such as a human, either locally or systemically.

The present invention provides methods to treat and/or prevent diseases, syndromes and/or conditions exacerbated by or involving the increased generation of PARP. These methods involve application or administration of the compounds of the present invention to cells, tissues, organs or organ systems of a person in need of such treatment or prevention.

In another embodiment the compounds and compositions of the present invention can be used to treat or prevent cell damage or death clue to necrosis or apoptosis, cerebral ischemia and reperfusion injury or neurodegenerative diseases in an animal, such as a human.

In another embodiment the compounds and compositions of the present invention can be used to extend the lifespan and proliferative capacity of cells and thus can be used to treat or prevent diseases associated therewith.

In another embodiment, the present invention provides methods of treating or preventing or ameliorating the effect of cancer and/or to radiosensitize tumor cells or hypoxic tumor cells to render the tumor cells more susceptible to radiation therapy and thereby to prevent the tumor cells from recovering from potentially lethal damage of DNA after radiation therapy. A method of this embodiment is directed to specifically and preferentially radiosensitizing tumor cells rendering the tumor cells more susceptible to radiation therapy than non-tumor cells.

The present invention also provides diazabenzo[de]anthracen-3-one compounds of Group I to treat, prevent and/or ameliorate the effects of cancers by potentiating the cytotoxic effects of ionizing radiation and/or chemotherapeutic agents on tumor cells.

In one embodiment the invention provides a chemosensitization method for treating cancers and or tumors comprising contacting the tumor or cancer cells with a cytotoxicity-potentiating diazabenzo[de]anthracen-3-one compound of Group I and further contacting the tumor or cancer cells with au anticancer agent.

The present invention provides a chemosensitization method for treating cancers in a mammal, particularly a human, comprising administering to the mammal diazabenzo[de]anthracen-3-one compound selected from Group I.

In one embodiment of the invention, the compound for use in the chemosensitization method of the invention is

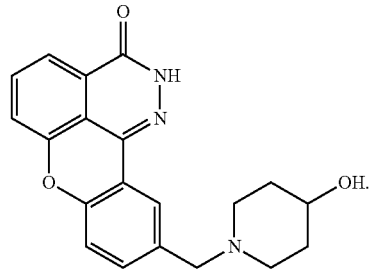

In another embodiment the present invention provides a chemosensitization method wherein a first dose of at least one compound of Group I is administered singly or repeatedly to a patient in need thereof and wherein subsequently a second dose of at least one chemotherapeutic agent is administered singly or repeatedly to said patient after a time period to provide an effective amount of chemosensitization.

In another embodiment the present invention provides a pt alma formulation comprising the chemosensitizing diazabenzo[de]anthracen-3-one derivative in a or selected from the group consisting of pharmaceutically acceptable free bases, salts, hydrates, esters, solvates, prodrugs, metabolites, stereoisomers, and mixtures thereof. According to a further embodiment, the pharmaceutical formulation further comprises a pharmaceutically acceptable carrier and, optionally, a chemotherapeutic agent. Non-limiting examples of such chemotherapeutic agents are recited below.

According to another embodiment of the invention, the chemosensitizing compound and the chemotherapeutic agent are administered essentially simultaneously.

According to another embodiment of the invention, the chemotherapeutic agent is selected from the group consisting of temozolomide adriamycin, camptothecin, carboplatin, cisplatin, daunorubicin, docetaxel, doxorubicin, interferon (alpha, beta, gamma), interleukin 2, irinotecan, paclitaxel, a taxoid, dactinomycin, daunorubicin, 4'-deoxydoxorubicin, Neomycin, pileamycin, mitomycin, neomycin and gentamycin, etoposide, 4-OH cyclophosphamide, a platinum coordination complex, topotecan, therapeutically elective analogs and derivatives of the same, and mixtures thereof. According to a preferred aspect the chemotherapeutic agent is temozolomide.

In one embodiment the present invention provides a pharmaceutical composition comprising a chemosensitizing effective amount of at least one diazabenzo[de]anthracen-3-one compound selected from Group I. In another aspect, the pharmaceutical composition comprises

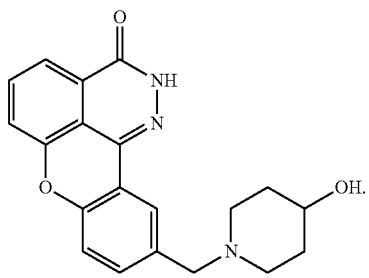

BRIEF DESCRIPTION OF THE DRAWINGS

FIG. I demonstrates that in mice bearing B16 melanoma, the mean survival time of the groups treated with compound 4i+TMZ combination was significantly higher than that Observed in animals receiving PAZ as single agent.

FIG. II shows that the combination treatment of Compound 4i+TMZ significantly reduced the growth of B16 melanoma (P<0.01 from day 9 to day 23, vs TMZ alone).

DETAILED DESCRIPTION OF THE INVENTION

Definitions

The present invention relates to the use of compounds of the present invention in the preparation of a medicament for the treatment of any disease or disorder in an animal or mammal described herein.

As used norm, "alkyl" means a branched or unbranched saturated hydrocarbon chain comprising a designated number of carbon atoms. For example, $C_1$-$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" means a branched or unbranched unsaturated hydrocarbon chain comprising a designated number of carbon atoms. For example, $C_2$-$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy", means the group —OR wherein R is alkyl as herein defined. R can also be a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

"Amino" compounds include amine ($NH_2$) as well as substituted amino.

"Ar", "aryl" or "heteroaryl" means a moiety which is substituted or unsubstituted, especially a cyclic or fused cyclic ring, and includes a mono-, bi-, or tricyclic, carbo- or heterocyclic ring, wherein the ring is either unsubstituted or substituted in one to five position(s) with halo, haloalkyl, hydroxyl, nitro, trifluoromethyl, $C_1$-$C_6$ straight or branched chain alkyl, $C_2$-$C_6$ straight or branched chain alkenyl. $C_1$-$C_6$ alkoxy. $C_2$-$C_6$ alkenyloxy, phenoxy, benzyloxy, amino, thiocarbonyl, ester, thioester, cyan, alkylamino, aminoalkyl, sulfhydryl, thioalkyl, and sulfonyl; wherein the individual ring sizes are 5-8 members; wherein the heterocyclic ring contains 1-4 heteroatom(s) selected from the group consisting of O, N, or S; wherein aromatic or tertiary alkyl amines are optionally oxidized to a corresponding N-oxide. Heteroaryls may be attached to other rings or substituted through the heteroatom and/or carbon atom of the ring. Aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Phenyl" includes all possible isomeric phenyl radicals, optionally monosubstituted or multi-substituted with substituents selected from the group consisting of amino, trifluoromethyl, $C_1$-$C_6$ straight or branched chain alkyl, $C_2$-$C_6$, straight or branched chain alkenyl, carbonyl, thiocarbonyl, ester, thioester, alkoxy, alkenoxy, cyano, nitro, imino, alkylamino, aminoalkyl, sulfhydryl, thioalkyl, hydroxy, halo, haloalkyl, $NR_2$ wherein $R_2$ is selected from the group consisting of hydrogen, ($C_1$-$C_6$)-straight or branched chain alkyl, ($C_3$-$C_6$) straight or branched chain alkenyl or alkynyl, and ($C_1$-$C_4$) bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

Cycloalkyl optionally containing at least one heteroatom includes saturated $C_3$-$C_8$ rings, such as $C_5$ or $C_6$ rings, wherein at 1-4 heteroatoms selected from O, N or S may be optionally substituted for a carbon atom of the ring. Cycloalkyls optionally containing at least one heteroatom, as described above, may be substituted by or fused to at least one 5 or 6 membered aryl or heteroaryl. Other cycloalkyls containing a heteroatom include pyrrolidinyl, imidazolidinyl, pyrazolidinyl, piperidinyl, piperazinyl, morpholino and thiomorpholino.

The term "neurodegenerative diseases" includes, but is not limited, to Alzheimer's disease, Parkinson's disease and Huntington's disease.

The term "nervous insult" refers to any damage to nervous tissue and any disability or death resulting therefrom. The cause Of nervous insult may be metabolic, toxic, neurotoxic, iatrogenic, thermal or chemical, and includes without limitation, ischemia, hypoxia, cerebrovascular accident, trauma, surgery, pressure, mass effect, hemorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent a neurodegenerative disease or preventing further neurodegeneration in patients who are already suffering from or have symptoms of a neurodegenerative disease.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and (iii) relieving the disease, disorder or condition, i.e., causing regression of the disease, disorder and/or condition.

The term "neural tissue damage resulting from ischemia and reperfusion injury and neurodegenerative diseases" includes damage due to neurotoxicity, such as seen in vascular stroke and global and focal ischemia.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

The term "radiosensitizer", as used herein, is defined as a molecule, such as a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 10 mm), or microwave radiation (1 mm to 30 cm).

The term "chemosensitizer", as used herein, refers to the ability of the compounds of the invention to potentiate the antitumoral activity of chemotherapeutic agents. Such chemosensitization is useful, for example, to increase the tumor growth-retarding or -arresting effect of a given dose of a chemotherapeutic agent, or to improve the side-effect profile of a chemotherapeutic agent by allowing for reductions in its dose while maintaining its antitumoral efficacy.

Pharmaceutical Uses of the Invention

The present invention provides compounds, methods and pharmaceutical compositions for inhibiting the nuclear enzyme poly(adenosine 5'-diphospho-ribose) polymerase ["poly(ADP-ribose) polymerase" or "PARP", which is also referred to as ADPRT (NAD:protein (ADP-ribosyl transferase (polymerising)), pADPRT (poly(ADP-ribose) transferase) and PARS (poly(ADP-ribose) synthetase). Moreover, the present invention provides methods of using PARP inhibitors of the invention to prevent and/or treat tissue damage resulting from cell damage or death due to necrosis or apoptosis; neural tissue damage resulting from, for example, ischemia and reperfusion injury, such as cerebral ischemic stroke, head trauma or spinal cord injury; neurological disorders and neurodegenerative diseases, such as, for example. Parkinson's or Alzheimer's diseases and multiple sclerosis; to prevent or treat vascular stroke; to treat or prevent cardiovascular disorders, such as, for example, myocardial infarction; to treat other conditions and/or disorders such as, for example, age-related muscular degeneration, AIDS and other immune senescence diseases, arthritis, atherosclerosis, ataxia telangiectasia, cachexia, cancer, degenerative diseases of skeletal muscle involving replicative senescence, diabetes (such as diabetes mellitus), inflammatory bowel disorders (such as colitis and Crohn's disease), acute pancreatitis, mucositis, hemorrhagic shock, splanchnic artery occlusion shock, multiple organ failure (such as involving any of the kidney, liver, renal, pulmonary, retinal, pancreatic and/or skeletal muscle systems), acute autoimmune thyroiditis, muscular dystrophy, osteoarthritis, osteoporosis, chronic and acute pain (such as neuropathic pain), renal failure, retinal ischemia, septic shock (such as endotoxic shock), local and/or remote endothelial cell dysfunction (such are recognized by endo-dependent relaxant responses and up-regulation of adhesion molecules), inflammation and skin aging; to extend the lifespan and proliferative capacity of cells, such as, for example, as general mediators in the generation of oxidants, proinflammatory mediators and/or cytokines, and general mediators of leukocyte infiltration, calcium ion overload, phospholipid peroxidation, impaired nitric oxide metabolism and/or reduced ATP production; to alter gene expression of senescent cells; or to radiosensitize hypoxic tumor cells.

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; and can radiosensitize cells. Generally, inhibition of PARP activity spares the cells from energy loss, preventing, in the case of neural cells, irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, arthritis, atherosclerosis, ataxia telangiectasia, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such neuropathic pain), renal failure, retinal ischemia, septic shock (such as endotoxic shock), and skin aging; to extend the lifespan and proliferative capacity of cells; to alter gene expression of senescent cells: or to radiosensitize hypoxic tumor cells. The present invention also relates to treating diseases and conditions in an animal which comprises administering to said animal a therapeutically effective amount of the above-identified compounds.

The present invention relates to a method of treating, preventing or inhibiting a neurological disorder in an animal, which comprises administering to said animal a therapeutically effective amount of the above-identified compounds. In a another embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another embodiment is when the reperfusion injury is a vascular stroke. Yet another embodiment is when the peripheral neuropathy is caused by Guillain-Barre syndrome. Still another embodiment is when the demyelinating disease and neurological disorder relates to neurodegeneration. Another embodiment is when the reperfusion injury is a vascular stroke. Still another preferred embodiment is when the demyelinating disease is multiple sclerosis. Another embodiment is when the neurological disorder relating to neurodegeneration is selected from the group consisting of Alzheimer's Disease, Parkinson's Disease, and amyotrophic lateral sclerosis.

Another embodiment is a method of treating, preventing or inhibiting a cardiovascular disease in an animal, such as angina pectoris, myocardial infarction, cardiovascular ischemia, and cardiovascular tissue damage related to PARP activation, by administering to said animal an effective amount of the compounds of the present invention.

The present invention also contemplates the use of a compound the present invention for inhibiting PARP activity, for treating, preventing or inhibiting tissue damage resulting front cell damage or death due to necrosis or apoptosis, for treating, preventing or inhibiting a neurological disorder in an animal.

In anther embodiment, the neurological disorder is selected from the group consisting of peripheral neuropathy caused by physical injury or disease state, traumatic brain injury, physical damage to the spinal cord stroke associated with brain damage, focal ischemia, global ischemia, reperfusion injury, demyelinating disease and neurological disorder relating to neurodegeneration.

Another embodiment is when the reperfusion injury is a vascular stroke. Yet another embodiment is when the peripheral neuropathy is caused by Guillain-Barre syndrome. Still another embodiment is when the demyelinating disease is multiple sclerosis. Another embodiment is when the neurological disorder relating to neurodegeneration is selected from the group consisting of Alzheimer's Disease, Parkinson's Disease, and amyotrophic lateral sclerosis.

The present invention also contemplates the use of a compound of the present invention in the preparation of a medicament for the treatment of any of the diseases and disorders in an animal described herein.

In another embodiment, the disease or disorder is a neurological disorder.

In another embodiment, the neurological disorder is selected from the group consisting of peripheral neuropathy caused by physical injury or disease state traumatic brain injury, physical damage to the spinal cord, stroke associated with brain damage, focal ischemia, global ischemia, reperfusion injury, demyelinating disease and neurological disorder relating to neurodegeneration. Another embodiment is when the reperfusion injury is a vascular stroke. Yet another embodiment is when the peripheral neuropathy is caused by Guillain-Barre syndrome.

Still another embodiment is when the demyelinating disease is multiple sclerosis. Another embodiment is when the neurological disorder relating to neurodegeneration is selected from the group consisting of Alzheimer's Disease, Parkinson's Disease, and amyotrophic lateral sclerosis.

In another embodiment of the present invention, a person diagnosed with acute retinal ischemia or acute vascular stroke is immediately administered, parenterally, either by, intermittent or continuous intravenous administration, a compound of the present invention either as a single dose, or a series of divided doses of the compound. After this initial treatment, and depending on the persons presenting neurological symptoms, the person optionally may receive the same or a different compound of the invention in the form of another parenteral dose. The compound of the invention can be administered by intermittent or continuous administration via implantation of a biocompatible biodegradable polymeric matrix delivery system containing the compound, or via a subdural pump inserted to administer the compound directly to the infarct area of the brain.

In another embodiment, the present invention provides methods to extend the lifespan and proliferative capacity of cells, such as, for example, in using the compounds of the invention as general mediators in the generation of oxidants, proinflammatory mediators and/or cytokines, and/or general mediators of leukocyte infiltration, calcium ion overload, phospholipid peroxidation, impaired nitric oxide metabolism and/or reduced ATP production Further still, the methods of the invention can be used to treat cancer and to radiosensitize tumor cells. The term "cancer" is interpreted broadly. The compounds of the present invention can be "anti-cancer agents", which term also encompasses "anti-tumor cell growth agents" and "anti-neoplastic agents". For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The methods of the present invention can also treat cancer in a mammal with an effective amount of temozolomide and a compound of the present invention. The cancer can be melanoma, lymphoma, and glioblastoma multiforme.

Radiosensitizers are known to increase the sensitivity of cancerous cells to the toxic effects of electromagnetic radiation. Several mechanisms thr the mode of action of radiosenstmers have been suggested in the literature including: hypoxic cell radiosensitizers (e.g., 2-nitroimidazole compounds, and benzotriazine dioxide compounds) promote the reoxygenation of hypoxic tissue and/or catalyze the generation of damaging oxygen radicals; non-hypoxic cell radiosensitizers halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BudR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives. Photofrin, benzoporphyrin derivatives, NPe6, tin etioporphyrin SnET2, pheoborbide-a, bacteriochlorophyll-a, naphenalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5' deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

The present invention provides means to treat chemotherapy-induced peripheral neuropathy. According to an aspect of the invention, the compounds of the present invention are administered prior to, or together with, the administration of at least one chemotherapy agent to prevent the development of neuropathy symptoms or to mitigate the severity of such symptoms. According to a further aspect, the compounds of the present invention are administered after the administration of at least one chemotherapeutic agent to cure a patient of the symptoms of neuropathy or to mitigate the severity of such symptoms, in another aspect, the present invention provides a method to retard, delay, or arrest the growth of tumor cells in a mammal, comprising the administration of a chemotherapeutic agent, and further comprising the administration of a compound of Group I in an amount sufficient to potentiate the antitumor activity of said chemotherapeutic agent.

In another embodiment compounds of the invention act as PARP inhibitors to treat or prevent cancers by chemopotentiating the cytotoxic effects of other chemotherapeutic agents.

The present invention provides compounds of Group I, derivatives thereof, and compositions containing these compounds to treat, prevent and/or ameliorate the effects of cancers by potentiating the cytotoxic effects of ionizing radiation on tumor cells.

In another embodiment the present invention provides compounds described herein, derivatives thereof, and compositions containing these compounds to treat, prevent, and/or ameliorate the effects of cancers by potentiating the cytotoxic effects of chemotherapeutic agents on tumor cells.

In another embodiment the methods of the invention can be used to treat cancer and to chemosensitize tumor cells. The term "cancer," as used herein, defined broadly. The compounds of the present invention can potentiate the effects of "anti-cancer agents," which term also encompasses "anti-tumor cell growth agents," "chemotherapeutic agents," "cytostatic agents," "cytotoxic agents," and "anti-neoplastic agents".

In one embodiment methods of the invention are useful for treating cancers and radiosensitizing or chemosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chrome lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The present invention provides a chemosensitization method for treating tumor and/or cancer cells comprising contacting said cancer cells with a diazabenzo[de]anthracen-3-one compound of Group I and further contacting said cancer cells with an anticancer anent.

Specific embodiments of the present invention de the diazabenzo[de]anthracen-3-one compounds shown in Group I and neutral and/or salt forms thereof, as well as enantiomer and racemic mixtures thereof, where appropriate.

The compounds of the present invention may possess one or more asymmetric center(s) and thus can be produced as mixtures (racemic and non-racemic) of stereoisomers, or as individual enantiomers or diastereomers. The individual stereoisomers may be obtained by using an optically active staring material, by resolving a racemic or non-racemic mixture of an intermediate at some appropriate stage of the synthesis, or by resolution of the compound of Group I. It is understood that the individual stereoisomers as well as mixtures (racemic and non-racemic) of stereoisomers are encompassed by the scope of the present in invention.

The compounds of the invention are useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the limn of pharmaceutically acceptable stereoisomers. These forms are all within the scope of the invention.

"Pharmaceutically acceptable salt", "hydrate", "ester" or "solvate" refers to a salt, hydrate, ester, or solvate of the inventive compounds which possesses the desired pharmacological activity and Which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxy-methyl)aminoethane; and the like. See, for example, "Pharmaceutical Salts," J. Pharm. Sci., 66:1, 1-19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a compound of the present invention in an aqueous or an aqueous alcohol solution or other suitable solvent containing the appropriate acid or base, and isolating the salt by evaporating the solution. Alternatively, the free base of a compound of the present invention can be reacted with an acid, as well as reacting a compound of the present invention having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g. toxicity). The prodrug can be readily prepared from the inventive compounds using methods known in the art, such as those described by Burgers Medicinal Chemistry and Drug Chemistry, Fifth Ed, Vol. 1, pp. 172-178, 949-982 (1995). For example, the inventive compounds can be transformed into prodrugs by converting one or more of the hydroxy or carboxy groups into esters.

"Pharmaceutically acceptable metabolite" refers to drugs that have undergone a metabolic transformation, After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect, For example, anticancer drugs of the antimetabolite class must be converted to their active forms after the have been transported into a cancer cell. Since most drugs undergo metabolic transformation of some kind, the biochemical reactions that play a role in drug metabolism may be numerous and diverse. The main site of drug metabolism is the liver, although other tissues may also participate.

Pharmaceutical Compositions of the Invention

The present Invention also relates to a pharmaceutical composition comprising a) a therapeutically effective amount of a compound of a diazabenzo[de]anthracen-3-one derivative and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form, The term parenteral used herein includes subcutaneous, intravenous, intramuscular, intraperitoneal, intrathecal intraventricular, intrasternal and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline. Ringer's solution, dextrose solution, isotonic sodium chloride solution, and Flanks solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., anti-oxidants, buffers and preservatives.

Formulations suitable for nasal or buccal administration as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the compound of Group I. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent Molded tablets may be made by molding in a suitable machine, a mixture of the powdered active ingredient and a suitable carrier moistened with an inert liquid diluent.

The compounds of this invention may also be administered rectally in the term of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant, or externally applied patch, suitable for providing efficacious concentrations of the PARP inhibitors over a prolonged period of time without the need for frequent re-dosing. Such controlled, release films are well known to the art. Particularly preferred are transdermal delivery systems. Other examples of polymers commonly employed for this purpose that may be used in the present invention include nondegradable ethylene-vinyl acetate copolymer a degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

In a preferred embodiment, the carrier is a solid biodegradable polymer or mixture of biodegradable polymers with appropriate time release characteristics and release kinetics. The corn position of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into to solid implant In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The compounds of the invention are used in the composition in amounts that are therapeutically effective. The compositions may be sterilized and/or contain adjuvants, such as preserving, stabilizing, welling, or emulsifying agents, solution promoters, salts for regulating, the osmotic pressure, and/or buffers. In addition, they may also contain other therapeutically valuable substances, such as, without limitation, the specific chemotherapeutic agents recited herein. The compositions are prepared according to conventional mixing, granulating, or coating methods, and contain about 0.1 to 75% by weight, preferably about 1 to 50% by weight, of the compound of the invention.

To be effective therapeutically as central nervous system targets, the compounds of the present invention should readily penetrate the blood-brain barrier when peripherally administered, Compounds which cannot penetrate the blood-brain barrier can be effectively administered by an intraventricular route or other appropriate delivery system suitable for administration to the brain.

For medical use, the amount required of the active ingredient to achieve a therapeutic effect will vary with the particular compound, the route of administration, the mammal under treatment, and the particular disorder or disease being treated. A suitable systematic, dose of a compound of the present invention or a pharmacologically acceptable salt thereof for a mammal suffering from, or likely to suffer from, any of condition as described hereinbefore b in the range of about 0.1 mg/kg to about 100 mg/kg of the active ingredient compound, the most preferred dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian can, for example, employ an intravenous bolus followed by an intravenous infusion and repeated administrations, parenterally or orally, as considered appropriate. While it is possible for an active ingredient to be, administered alone, it is preferable to present it as a formulation.

When preparing dosage form incorporating the compositions of the invention, the compounds may also be blended with conventional excipients such as hinders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbents, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

The present invention relates to the use of a compound of Group I in the preparation of a medicament for the treatment of any disease or disorder in an animal described herein, in an embodiment, the compounds of the present invention are used to treat cancer, in a preferred embodiment, the compounds of the present invention are used to potentiate the cytotoxic effects of ionizing radiation, in such an embodiment, the compounds of the present invention act as a radiosensitizer. In an alternative preferred embodiment, the compounds of the present invention are used to potentiate the cytotoxic effects of chemotherapeutic agents. In such an embodiment, the compounds of the present invention act as a chemosensitizer.

Any pharmacologically-acceptable chemotherapeutic agent that acts by damaging DNA is suitable as the chemotherapeutic agent of the present invention, in particular, the present invention contemplates the use of a chemotherapeutically effective amount of at least one chemotherapeutic agent including, but not limited to: temozolomide, adriamycin, camptothecin, carboplatin, cisplatin, daunorubicin, docetaxel, doxorubicin, interferon (alpha, beta, gamma), interleukin 2, irinotecan, paclitaxel topotecan, therapeutically effective analogs and derivatives of the same, and mixtures thereof, According to a preferred aspect, the chemotherapeutic agent is temozolomide.

The disclosure contained herein demonstrates the usefulness of the compounds and compositions of the present invention in treating and/or preventing cancer, such as by radiosensitizing and/or chemosensitizing tumor and/or cancer cells to chemotherapeutic agents.

EXAMPLES

The diazabenzo[de]anthracen-3-one compounds of the present invention can be synthesized using the starting materials and methods disclosed in U.S. 60/644,584, which is incorporated herein by reference in its entirety for all purposes.

Some of the PARP inhibitors used in the inventive methods and pharmaceutical compositions can be readily prepared by standard techniques of organic chemistry, utilizing the general synthetic pathways and examples depicted in publications. See, e.g., Wu et al, "The Protective Effect of GPI 18078, a Novel Water Soluble Poly (ADP-Ribose) Polymerase Inhibitor in Myocardial Ischemia Reprefusion Injury, Experimental Biology," FASEB April 11-15 (2003); Wu et al., "Myocardial Protection and Anti-Inflammatory Effect of GPI 15427, a Novel Water Soluble Poly (ADP-Ribose) Polymerase Inhibitor: Comparison with GPI 6150, Experimental Biology," FASEB, April 11-15 (2003); Kalish et al., "Design, Synthesis and SAR of PARP-1 Inhibitors, ISMC Meeting, Barcelona," Sep. 4, 2002; Xu et al., "Design and Synthesis of Novel Potent Poly (ADP-Ribose) Polymerase (PARE) Inhibitors. 224th ACS National Meeting," Boston, August 18-23 (2002); Williams et al., "Intravenous Delivery of GPI 15427/C and GPI 16519/C. Potent Water-Soluble PARE Inhibitors, Reduces Infarct Volume Following Permanent and Transient Focal Cerebral Ischemia, Society for Neuroscience," Orlando Fla., October (2002); Tentori L, et al., "Systemic administration of the PARE-1 inhibitor GPI 15427 increases the anti-tumor activity of temozolomide against metastatic melanoma," *Medical Science Monitor, Vol. 9*, supplement 1, 34 (2003); Tentori et al., "Poly(ADP-Ribose) Polymerase inhibitor to Increase Temozolomide Efficacy Against Melanoma, Glioma and Lymphoma at the CNS Site," AACR poster, April (2003); Suto et. al., "Dihydroiso-quinolinones: The Design and Synthesis of a New Series of Potent inhibitors of Poly(ADP-ribose) Polymerase," *Anticancer Drug Des.,* 6; 107-17 (1991); and U.S. Pat. Nos. 6,348,475, 6,545,011, RE36,397, 6,380,211, 6,235,748, 6,021,278, 6,197,785, 6,380,193, 6,346,536, 6,514,983, 6,306,889, 6,387,902, 6,201,020, and 6,291,425, and U.S. patent application Ser. No. 10/853,714, the entire contents of which patents, patent application and publications are herein incorporated by reference, as though set forth herein in full.

The compounds of this invention can be prepared in a conventional manner as illustrated below in Schemes 1. Starting derivatives are known in the chemistry literature and accessible by processes known to one skilled in the art.

Scheme 1

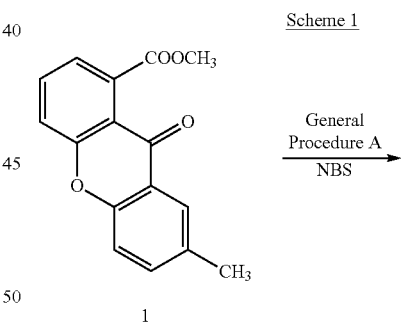

General Procedure A
NBS

1

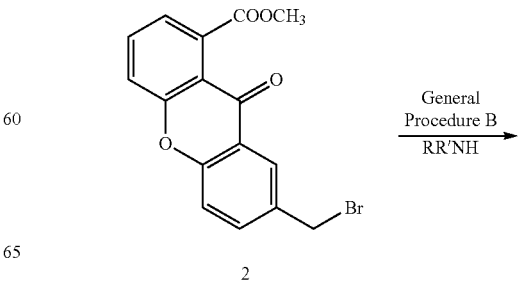

General Procedure B
RR'NH

2

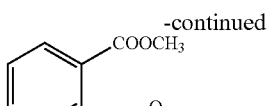

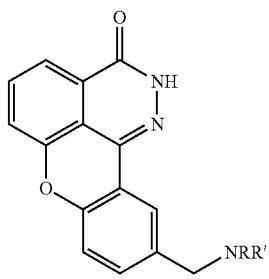

Example 4 a-s

General Procedure A

Preparation of 7-bromomethyl-9-oxoxanthene-1-carboxylic acid methyl ester

Brominating agents including N-bromosuccinimide, bromine and complexed bromine such as pyridinium bromide can be used to convert 7-methyl-9-oxoxanthene-1-carboxylic acid methyl ester, 1, to 7-bromomethyl-9-oxoxanthene-1 carboxylic acid methyl ester, 2. Suitable solvents include, but are not limited to, chlorinated hydrocarbons, polar aprotic solvents, as well as various ethers. Temperatures are generally between 0 and 100° C., with a range of 50-70° C. being preferred.

Example 1

To a stirred solution of compound 5 (400 g, 1.49 mol) in refluxing carbon tetrachloride (10 L) containing benzoyl peroxide (10 g, 0.041 mol) was added NBS (292 g, 1.64 mol) in several portions over 45 minutes. The resulting mixture was refluxed for 12 hours and then cooled to room temperature overnight. The precipitated was filleted off and the cake was washed with water (1.2 L) thoroughly and dried to give 322 g of compound 6 as a white solid (62%).

Example 2

To a solution of compound 1 (1.97 g, 7.3 mmol, 1.00 eq) in carbon tetrachloride (400 mL) was added N-bromosuccinimide (1.44 g, 8.1 mmol, 1.10 eq) and a catalytic amount of benzoyl peroxide (45 mg, 0.2 mmol, catalytic). The reaction mixture was heated to reflux for 6 hours and then cooled to room temperature. The resulting white precipitate was isolated via vacuum filtration. Residual solvents were removed and the filter cake was twice recrystallized from ethyl acetate and hexanes to yield a white solid, 2. (1.15 g, 45%). $^1$H NMR (400 MHz, CDCl$_3$) 8.27 (d, J=2.5 Hz, 1H), 7.72-7.80 (m, 2H), 7.57 (dd, J=8.5 and 10.1 Hz, 1H), 7.48 (d, J=8.5 Hz, 1H), 7.33 (dd, J=7.0 and 1.1 Hz, 1H), 4.57 (s, 2H), 4.00 (s, 3H), $^{13}$C NMR (400 MHz, CDCl$_3$) 31.97, 53.06, 118.63, 118.71, 119.63, 121.56, 122.81, 126.83, 134.15, 134.18, 134.50, 135.95, 155.31, 155.87, 169.77, 175.48.

General Procedure B

Preparation of substituted 9-oxoxanthene-1-carboxylic acid methyl esters

The primary bromide in compound 2 can be readily displaced by nucleophiles which include primary and secondary amines and is preferably done so in the presence of a non-reactive basic species, such as potassium carbonate. Suitable solvents for this transformation are polar and aprotic such as dimethylformamide or acetonitrile, but the reaction may also be performed in other media. The temperature may range from 0-100° C. with 50-80° C. being preferred.

Example 1

To a solution of compound 2 (3.47 g, 10.0 mmol, 1.00 eq) in dimethylformamide (100 mL) is added potassium carbonate (13.82 g, 100.0 mmol, 10.00 eq) and a secondary amine (10 mmol, 1 eq). The reaction mixture is heated to 70'C. for 6 hours and then cooled to room temperature, Water (100 mL) is added to the reaction mixture, followed by ethyl acetate (200 mL). The organic layer is collected, washed with water followed by brine and then dried over sodium or magnesium sulfate. The solvents are removed In vacuo and the residue is purified by column chromatography using ethyl acetate and hexanes as an eluent to give product 3 in 50-90% yields.

Example 2

To a solution of compound 2 (1.53 g, 4.4 mmol, 1.00 eq) in acetonitrile (50 mL) was added potassium carbonate (1.2 g, 8.7 mmol, 2.00 eq) and 1-methylpiperazine (0.51 mL, 4.6 mmol, 1.05 eq). The reaction mixture was then heated to reflux overnight. After cooling to room temperature, the solids were removed by filtration and the organics were evaporated to an oily residue. This material was dissolved in ethyl acetate (150 ml) and extracted with 1 N HCl (150 ml). The organic layer was discarded and the pH of the aqueous layer was adjusted to greater than 9 with 6 N sodium hydroxide. The product was then extracted with two portions of ethyl acetate (100 ml) which were subsequently combined, washed successively with water and brine and then dried over magnesium sulfate, All solvents were removed in vacuo to afford 3a as a white solid. (0.95 g, 59%), $^1$H NMR (400 MHz, CDCl$_3$) of 3a: 8.18 (d, J=2.5 Hz, 1H), 7.71-7.75 (m, 2H), 7.56 (dd, J=8.5 and 1.1 Hz, 1H), 7.45 (d, J=8.5 Hz, 1H), 7.32 (dd, J=7.0 and 1.1 Hz, 1H), 4.04 (s, 3H), 3.58 (s, 2H), 2.45 (br, 8H), 2.27 (s, 3H).

General Procedure C

Preparation of 10-aminomethyl-2H-7-oxa-1,2-diaza-benzo[de]anthracen-3-one derivatives Cyclization of the ketone and methyl ester in compound 3 to form benzopyrano[4,3,2-de]phthalazine rings can be performed with hydrazine to afford 10-aminomethyl-2H-7-oxa-1,2-diaza-benzo[de]anthracen-3-one derivatives, 4, in high yield. Ethanol is the preferred solvent, but the reaction is not exclusively limited to this media. Temperatures can range from 0-120° C., with 70-90° C. being most desirable.

Example 1

To a solution of 3 (5 mmol) m absolute ethanol (10 mL) is added anhydrous hydrazine in ethanol (1 mL) drop wise at room temperature. After the addition is complete, the solution is heated to reflux overnight. Once cooled to room temperature, ice-cold water (100 mL) is added and white solid is precipitated. The solid is collected b vacuum filtration, washed successively with water and ethanol and then dried in vacuo to afford 4 as a white solid (40-85% yield).

Example 2

7-(1,4-Dioxa-8-aza-spiro[4.5]dec-8-ylmethyl)-9-oxo-9H-xanthene-1-carboxylic acid methyl ester, 3n (1.6 g, 3.91 mmol, 1 eq), in ethanol (55 ml) was heated to 80° C. and stirred until all material was in solution, To this hydrazine monohydrate (20 ml, large excess) was added dropwise over ten minutes. The reaction mixture was heated to reflux overnight during which time a heavy white precipitate formed. The solution is allowed to cool to room temperature and product is isolated by vacuum filtration. Washing with successive small portions of water, ethanol and pentane and then subsequent drying in vacuo affords 4n in high yield (1.4 g, 92%). $^1$H-NMR (DMSO-$d_6$, 300 MHz): 1.62 (t, J=5.0, 4H), 2.40-2.50 (m, 4H), 3.55 (s, 2H), 3.85 (s, 4H), 7.34 (d, J=9.4 Hz, 1H), 7.47 (d, J=7.5 Hz, 1H), 7.67-7.70 (m, 1H), 7.86-7.92 (m, 2H), 7.98 (s, 1H), 12.62 (s, 1H).

Compound 4a 10-(4-Isopropyl-piperazin-1-ylmethyl)-2H-7-oxa-1,2-diaza-benzo[de]anthracen-3-one

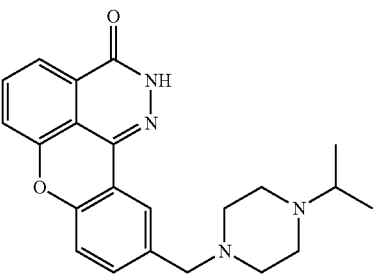

Prepared from compound 2 and 1-isopropyl-piperazine according to general procedures B and C. Purification of the product by crystallization from ethanol gave 4a as a white solid. MS (ES+): 377. $^1$H-NMR (CDCl$_3$, 300 MHz); 0.90-1.00 (m, 6H), 2.25-2.50 (m, 8H), 2.55-2.60 (m, 1H), 3.34 (s, 2H), 7.35 (d, 1H), 7.46 (d, 1H), 7.68 (dd, 1H), 7.80-7.95 (m, 2H), 7.95-8.05 (m, 1H), 12.63 (s, 1H). Anal. Calcd. for C$_{22}$H$_{24}$N$_4$O$_2$:C, 70.19; H, 6.43; N, 14.88. Found: C, 70.09; H, 6.51; N, 14.77.

Compound 4b

10-[4-(2-Methoxy-ethyl)-piperazin-1-ylmethyl]-2H-7-oxa-1,2-diaza-benzo[de]anthracen-3-one

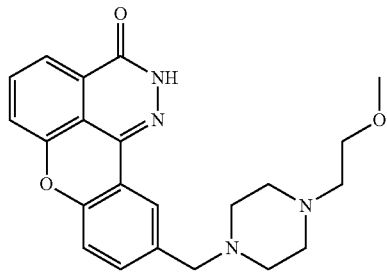

Prepared from compound 2 and 1-(2-methoxyethyl)piperazine according to general procedures B and C. Purification of the product by crystallization from ethanol gave 4b as a white solid, MS (ES+): 393; $^1$H-NMR DMSO-$d_6$, 300 MHz): 230-2.49 (m, 10H), 3.22 (s, 3H), 330-3.45 (m, 2H), 3.50 (m, 2H), 7.30-7.35 (m, 1H), 7.40-7.48 (m, 1H), 7.65-7.70 (m, 1H), 7.85-7.95 (m, 2H), 7.95-8.05 (m, 1H), 12.63 (s, 1H). Anal. Calcd. for C$_{22}$H$_{24}$N$_4$O$_3$: C, 67:33; H, 6.16; N, 14.28. Found: C, 67.35; H, 6.16; N, 14.45.

Compound 4c 10-(4-Pyrimidin-2-yl-piperazin-1-ylmethyl)-2H-7-oxa-1,2-diaza-benzo[de]anthracen-3-one

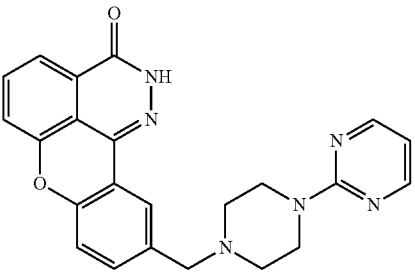

Prepared from compound 2 and 1-(2-pyrimidyl)piperazine according to general procedures b and C. Purification of the product by crystallization from ethanol gave 4c as a white solid. MS (ES+): 413. $^1$H-NMR (DMSO-$d_6$, 300 MHz): 3.28-3.34 (m, 4H), 3.60 (s, 2H), 3.70-338 (m, 4H), 6.60-6.62 (m, 1H), 7.38-7.40 (m, 1H), 7.50-7.60 (m, 1H), 7.70-7.74 (m, 1H), 7.80-7.95 (m, 2H), 8.05-8.10 (m, 830-8.40 (m, 2H), 12.64 (s, 1H). Anal. Calcd. for $C_{23}H_{20}N_6O_2$: C, 66.98; H, 4.89; N, 20.38. Found: C, 67.03; H, 4.88; N, 20.15.

Compound 4d 10-(3-Oxo-piperazin-1-ylmethyl)-2H-7-oxa-1,2,-diaza-benzo[de]anthracen-3-one

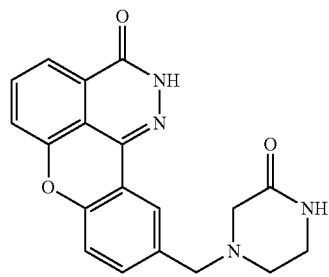

Prepared from compound 2 and piperasin-2-one according to general procedures B and C, Purification of the product by crystallization from ethanol gave 4d as a white solid. MS (ES+): 349; $^1$H-NMR (DMSO-$d_6$, 300 MHz): 2.58-2.62 (m, 2H), 2.94 (s, 2H), 3.16-3.20 (m, 2H), 3.63 (s, 2H), 730-7.35 (m, 1H), 7.40-7.48 (m, 1H), 7.65-7.70 (m, 1H), 7.85-7.95 (m, 2H), 7.95-8.05 (m, 1H).

Compound 4e

10-[4-(2-Pyrrolidin-1-yl-ethyl)-piperazin-1-ylmethyl]-2H-7-oxa-1,2,diaza-benzo[de]anthracen-3-one

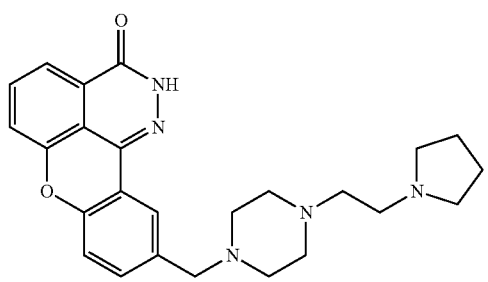

Prepared from compound 2 and 1-(2-Pyrrolidin-1-yl-ethyl)-piperazine according to general procedures B and C. Purification of the product by crystallization from ethanol gave 4e as a white solid. $^1$H-NMR (DMSO-$d_6$, 300 MHz); 1.64 (m, 4H), 2.30-2.55 (m, 16H), 3.52 (s, 2H), 7.30-7.40 (m, 1H), 7.45-7.50 (m, 1H), 7.70-7.75 (m, 1H), 7.80-7.90 (m, 2H), 8.00-8.05 (m, 1H). Anal. Calcd. for $C_{25}H_{29}N_5O_2 \cdot (0.7\ H_2O)$: C, 67.61; H, 6.90; N, 15.77; Found: C, 67.25; H, 6.81; N, 15.67.

Compound 4f

10-[4-(3-Dimethylamino-propyl)-piperazin-1-ylmethyl]-2H-7-oxa-1,2-diaza-benzo[de]anthracen-3-one

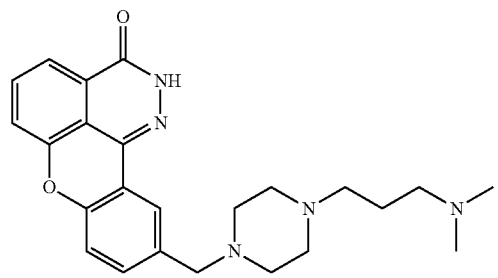

Prepared from compound 2 and Dimethyl-(3-piperazin-1-yl-propyl)-amine according to general procedures B and C. Purification of the product by crystallization from ethanol gave 4f as a white solid. $^1$H-NMR (DMSO-$d_6$, 300 MHz): 1.45-1.55 (m, 2H), 2.09 (s, 6H), 2.10-2.40 (m, 12H), 3.52 (s, 2H), 7.30-7.40 9 m, 1H), 7.40-7.50 (m, 1H), 7.70-7.75 (m, 1H), 7.80-7.95 (m, 2H), 8.01 (s, 1H).

Compound 4g

10-{[(2-Diethylamino-ethyl)-ethyl-amino]-methyl}-2H-7-oxa-1,2-diaza-benzo[de]anthracen-3-one

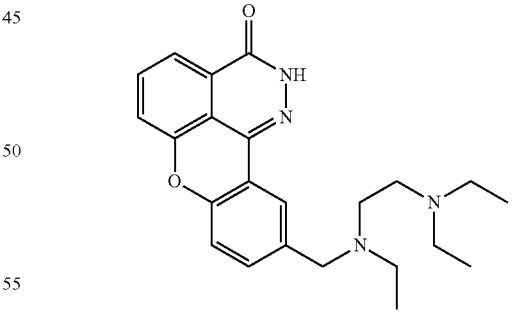

Prepared from compound 2 and N,N-Diethyl-M-ethyl-ethane-1,2-diamine according to general procedures 11 and C. Purification of the product by crystallization from ethanol gave 4g as a white solid. $^1$H-NMR (DMSO-d. 300 MHz): 0.90 (t, J=7.2 Hz, 6H), 1.00 (t, J=6.8 Hz, 3H), 2.41 (dd, J=14.3 and 7.2 Hz, 4H), 2.45-2.55 (m, 6H), 3.62 (s, 2H), 7.35 (d, J=8.6

Hz, 1H), 7.49 (dd, J=8.3 and 2.3 Hz, 1H), 7.69 (dd, J=7.1 and 2.4 Hz, 1H), 7.86-7.93 (m, 2H), 8.03 (d, J=2.3 Hz, 1H)

Compound 4h

10-{[(2-Diethylamino-ethyl)-methyl-amino]-methyl}-2H-7-oxa-1,2-diaza-benzo[de]anthracen-3-one

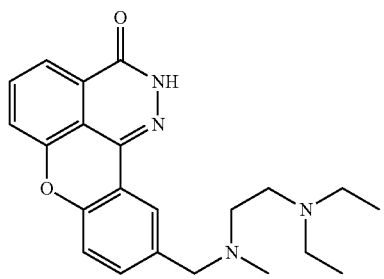

Prepared from compound 2 and N,N-Diethyl-N'-methyl-ethane-1,2-diamine according to general procedures B and C. Purification of the product by crystallization from ethanol gave 4h as a white solid. $^1$H-NMR (DMSO-d$_6$, 300 MHz): 12.63 (s, 1H) 8.00 (d, J=1.9 Hz, 1H), 7.91-7.80 (m, 2H), 7.70 (dd, J=7.1 and 2.0 Hz, 1H), 7.49 (dd, J=18.6 and 2.0 Hz, 1H), 7.36 (d, J=8.5 Hz, 1H), 3.55 (s, 2H), 3.88 (m, 4H), 2.47 (q, J=7.0 Hz, 4H), 2.17 (s, 3H), 0.93 (t, J=7.0 Hz, 6H), Anal. Calcd. for $C_{22}H_{26}N_4O_2$: C, 69.82; H, 6.92; N, 14.80; Found: C, 69.56; H, 6.95; N, 14.60.

Compound 4i 10-(4-Hydroxy-piperidin-1-ylmethyl)-2H-7-oxa-1,2-diaza-benzo[de]anthracen-3-one

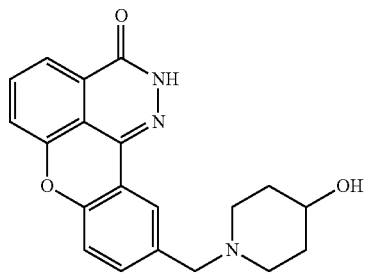

Prepared from compound 2 and Piperidin-4-ol according to general procedures B and C. Purification of the product by crystallization from ethanol gave 4i as a white solid. $^1$H-NMR (DMSO-d$_6$, 300 MHz): 12.60 (s, 1H), 7.96 (d, J=1.9 Hz, 1H), 7.91-7.84 (m, 2H), 7.66 (dd, J=6.9 and 2.3 Hz, 1H), 7.43 (dd, J=8.6 and 2.1 Hz, 1H), 7.32 (d, J=8.6 Hz, 1H), 4.54 (d, J=4.2 Hz, 1H), 3.48 (s, 2H), 3.46 (m, 1H), 2.65 (m, 2H), 2.05 (m, 2H), 1.68 (m, 2H), 1.40 (m, 2H). Anal. Calcd, for $C_{20}H_{19}N_3O_3$: C, 68.75; H, 5.48; N, 12.03; Found: C, 68.66; H, 5.48; N, 12.13.

Compound 4j

10-{[Ethyl-(2-hydroxy-ethyl)-amino]-methyl}-2H-7-oxa-1,2, diaza-benzo[de]anthracen-3-one

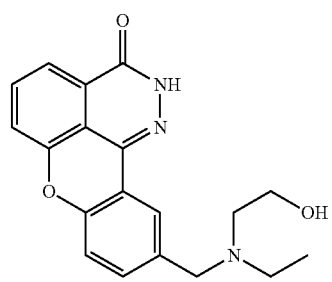

Prepared from compound 2 and 2-Ethylamino-ethanol according to general procedures B and C. Purification of the product by crystallization from ethanol gave 4j as a white solid. $^1$H-NMR (DMSO-d$_6$, 300 MHz): 1.00 (t, J=6.4 Hz, 3H), 2.45-2.55 (m, 4H), 3.49 (dd, J=12.0 and 5.5 Hz, 2H), 3.64 (s, 2H), 4.39 (t, J=5.1 Hz, 1H), 7.35 (d, J=8.5 Hz, 1H), 7.50 (dd, J=8.8 and 6.5 Hz, 1H), 7.69 (dd, J=6.5 and 4.3 Hz, 1H), 7.86-7.91 (m, 2H), 8.02 (d, J=2.0 Hz, 1H).

Compound 4k

10-[(Diisopropylamino)-methyl]-2H-7-oxa-1,2-diaza-benzo[de]anthracen-3-one

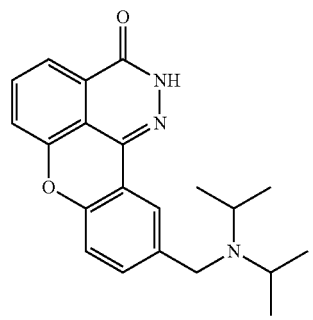

Prepared from compound 2 and diisopropylamine according to general procedures B and C. Purification of the product by crystallization from ethanol gave 4k as is white solid, $^1$H-NMR (DMSO-d$_6$, 300 MHz): 1.01 (d, J=6.3 Hz, 12H), 2.93 3.04 (m, 2H), 3.66 (s, 2H), 7.34 (d, J=8.4 Hz, 1H), 7.51

(dd, J=9.2 and 1.9 Hz, 1H). 7.69 (dd, J=6.5 and 2.7 Hz, 1H), 7.86-7.91 (m, 2H), 8.09 (d, J=1.9 Hz, 1H).

Compound 4l 10-(3-Hydroxy-pyrrolidin-1-ylmethyl)-2H-7-oxa-1, 2-diaza-benzo[de]anthracen-3-one

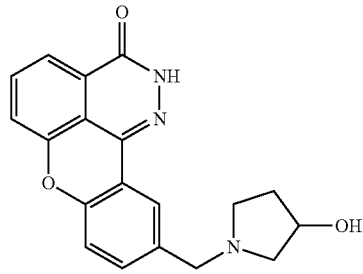

Prepared from compound 2 and Pyrrolidin-3-ol according to general procedures B and C. Purification of the product by crystallization from ethanol gave 4l as a white solid. $^1$H-NMR (DMSO-$d_6$, 300 MHz); 1.50-1.60 (m, 1H), 1.95-2.05 (m, 1H), 2.31-2.35 (m, 1H), 2.55-2.65 (m, 1H), 2.68-2.74 (m, 1H), 3.62 (d, J=4.2 Hz, 2H), 4.18-4.25 (m, 1H), 4.72 (d, J=4.5 Hz, 1H), 7.35 (d, J=8.6 Hz, 1H), 7.46-7.49 (m, 1H), 7.70 (dd, J=6.9 and 2.2 Hz, 1H), 7.87-7.91 (m, 2H), 8.00 (d, J=1.6 Hz, 1H). Anal. Calcd. for $C_{19}H_{17}N_3O_3$: C, 68.05; H, 5.11; N, 12.53; Found: C, 67.80; H, 5.11; N, 12.49.

Compound 4m

10-[4-(2-Hydroxy-ethyl)-piperidin-1-ylmethyl]-2H-7-oxa-1,2-diaza-benzo[de]anthracen-3-one

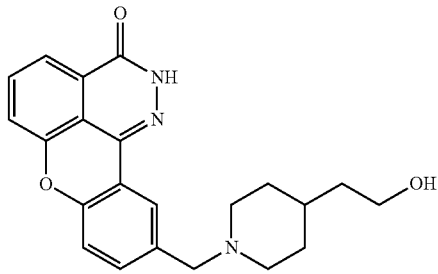

Prepared from compound 2 and 2-Piperidin-4-yl-ethanol according to general procedures B and C. Purification of the product by crystallization from ethanol nave 4m as a white solid. $^1$H-NMR (DMSO-$d_6$, 300 MHz): 1.12-1.17 (m, 2H), 1.34-1.38 (m, 3H), 1.61 (d, J=12 Hz, 1H), 1.92 (t, J=11 Hz, 2H), 2.80 (d, J=10.6 Hz, 2H), 3.42-3.48 (m, 4H), 4.34 (t J=5.2, 1H), 7.33 (d, J=8.8 Hz, 1H), 7.43-7.46 (m, 1H), 7.68 (dd, J=6.9 and 2.5 Hz, m), 7.86-7.98 (m, 3H). Anal. Calcd. for $C_{22}H_{23}N_3O_3$: C, 70.01; H, 6.14; N, 11.13; Found: C, 69.82; H, 6.12; N, 11.08.

Compound 4n 10-(1,4-Dioxa-8-aza-spiro[4.5]dec-8-ylmethyl)-2H-7-oxa-1,2-diaza-benzo[de]anthracen-3-one

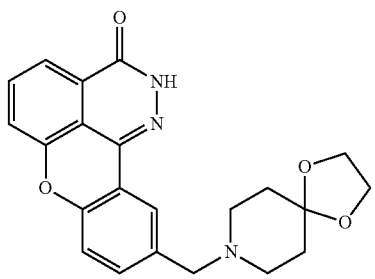

Prepared from compound 2 and 1,4-Dioxa-8-aza-spiro [4.5]decane according to general procedures B and C. Purification of the product by crystallization from ethanol gave 4n as a white solid. $^1$H-NMR (DMSO-$d_6$, 300 MHz): 1.62 (t, J=5.0, 4H), 2.40-2.50 (m, 4H), 3.55 (s, 2H), 3.85 (s, 4H), 7.34 (d, J=9.4 Hz, 1H), 7.47 (d, J=7.5 Hz, 1H), 7.67-7.70 (m, 1H), 7.86-7.92 (m, 2H), 7.98 (s, 1H), 12.62 (s, 1H). Anal. Calcd. for $C_{22}H_{21}N_3O_4$: C, 67.41; H, 5.43; N, 10.98; Found: C, 67.15; H, 5.30; N, 11.03.

Compound 4o 10-(3-Hydroxy-piperidin-1-ylmethyl)-2H-7-oxa-1,2-diaza-benzo[de]anthracen-3-one

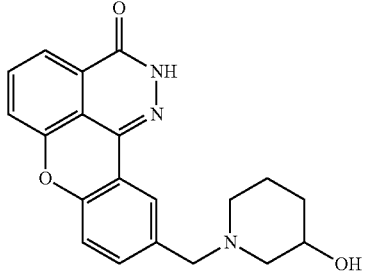

Prepared from compound 2 and piperidin-3-ol according to general procedures B and C. Purification of the product by crystallization from ethanol gave 4o as a white solid. $^1$H-NMR DMSO-$d_6$, 300 MHz): 1.00-1.12 (m, 1H), 1.30-1.50 (m, 1H), 1.52-1.95 (m, 4H), 2.66-2.83 (m, 2H), 3.45-3.60 (m, 3H), 4.60 (6, J=5.0 Hz, 1H), 7.34-7.48 (m, 2H), 7.68-7.70 (dd, J=6.8 and 2.2 Hz, 1H), 7.87-8.00 (m, 3H).

Compound 4p 10-(3-Hydroxy-azetidin-1-ylmethyl)-2H-7-oxa-1,2-diaza-benzo[de]anthracen-3-one

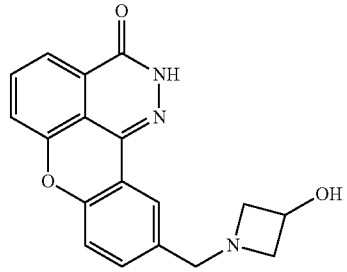

Prepared from compound 2 and azetidin-3-ol according to general procedures B and C. Purification of the product by crystallization from ethanol gave 4p as a white solid. $^1$H-NMR (DMSO-d$_6$, 300 MHz): 2.79 (t, J=6.9 Hz, 2H), 3.51 (t, J=6.3 Hz, 2H), 3.61 (s, 2H), 4.23 (dd, J=12.9 and 6.3 Hz, 1H), 5.33 (d, J=6.5 Hz, 1H), 7.33 (d, J=8.4 Hz, 1H), 7.71-7.44 (m, 1H), 7.68 (dd, J=6.8, 2.6, 1H), 7.86-7.96 (m, 3H), 12.62 (bs, 1H). Anal. Calcd. for C$_{18}$H$_{15}$N$_3$O$_3$.(0.5 H$_2$O): C, 65.45; H, 4.88; N, 12.72: Found: C, 65.06; H, 4.60; N, 13.03.

Compound 4q

10-[(2-Morpholin-4-yl-ethylamino)-methyl]-2H-7-oxa-1,2-diaza-benzo[de]anthracen-3-one

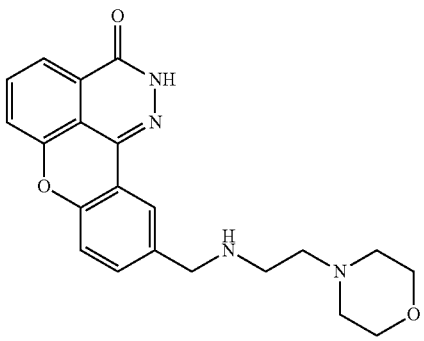

Prepared from compound 2 and 2-morpholin-4-yl-ethylamine according to general procedures B and C. Purification of the product by crystallization from ethanol gave 4q as a white solid. $^1$H-NMR (DMSO-d$_6$, 300 MHz): 2.16 (bs, 1H), 2.34 (bs, 4H), 2.40 (t, J=6.6 Hz, 2H), 2.60 (t, J=6.1 Hz, 2H), 3.56 (t, J=4.6 Hz, 4H), 3.76 (s, 2H), 7.33 (d, J=8.1 Hz, 1H), 7.48 (dd, J=8.3 and 1.8 Hz, 1H), 7.68 (dd, J=6.6 and 2.3, 1H), 7.88-7.93 (m 2H), 8.01 (d, J=1.5, 1H), 12.63 (bs, 1H). Anal. Calcd. For C$_{20}$H$_{19}$N$_3$O$_3$: C, 68.75; H, 5.48; N, 12.03; Found: C, 68.85; H, 5.48; N, 12.10.

Compound 4r

10-[(4-Hydroxy-cyclohexylamino)-methyl]-2H-7-oxa-1,2-diaza-benzo[de]anthracen-3-one

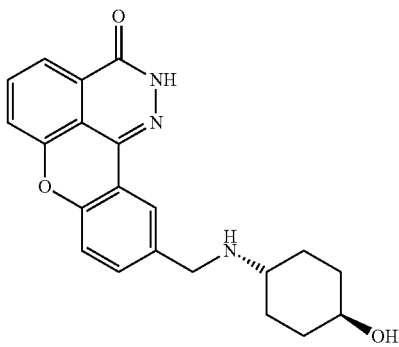

Prepared from compound 2 and trans-4-amino-cyclohexanol according to general procedures B and C. Purification of the product by crystallization from ethanol gave 4r as a white solid. $^1$H-NMR (DMSO-d$_6$, 300 MHz): 1.03-1.16 (m, 4H), 1.75-1.9 (m, 4H), 2.30-2.40 (m, 1H), 3.75 (s, 2H), 4.48 (d, J=3.4, 1H), 7.31 (d, J=8.1 Hz, 1H), 7.48 (dd, J=8.5 and 2.1 Hz, 1H), 7.67 (dd, J=6.8 and 2.4 Hz, 1H,) 7.85-7.92 (m, 2H), 8.02 (d, J=1.9 Hz, 1H). Anal. Calc. for C$_{21}$H$_{21}$N$_3$O$_3$.(0.5 H$_2$O).(0.5 N$_2$H$_4$); C, 67.44; H, 5.98; N, 11.61; Found: C, 67.56; H, 5.74; N, 11.68.

Calcd. for C$_{21}$H$_{22}$N$_4$O$_3$.(0.75 H$_2$O): C, 64.35; H, 6.04; N, 14.29; Found: C, 64.35; H, 5.91; N, 14.26.

Compound 4s 10-(4-Oxo-piperidin-1-ylmethyl)-2H-7-oxa-1,2-diaza-benzo[de]anthracen-3-one

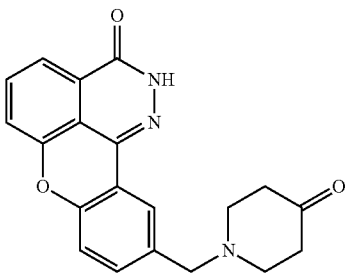

Compound 4n (100 mg, 0.2.4 mmol) was set stirring in acetic acid (3 ml) and to this at room temperature, was added concentrated HCl (0.6 ml, large excess). The reaction was heated to 90° C. for 1 hour and then cooled to room temperature. Product was isolated by extraction with ethyl acetate after basifying to pH 11-12 with 1N NaOH. Organics were dried over magnesium sulfate and concentrated in vacuo to afford 4s as a white solid (60 mg, 71%). $^1$H-NMR (DMSO-d$_6$, 300 MHz): 237 (t, J=2.4 Hz, 4H), 2.73 (t. J=2.7 Hz, 4H), 3.69 (s, 2H), 7.38 (d, J=8.5 Hz, 1H), 7.53 (dd, J=9.0 and 6.1 Hz), 7.70 (dd, J=7.1 and 4.7 Hz, 1H), 7.86-7.94 (m, 2H), 8.06 (d, J=2.4 Hz, 1H).

Other manners, variations or sequences of preparing the compounds of the present invention will be readily apparent to those skilled in the art.

The compounds of the present invention may be useful in the free base form, in the form of base salts where possible, and in the form of addition salts, as well as in the five acid form. All these forms are within the scope of this invention. In practice, use of the salt form amounts to use of the base form. Pharmaceutically acceptable salts within the scope of this invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like respectively, or those derived from bases such as suitable manic and inorganic bases. Examples of pharmaceutically acceptable base addition salts with compounds of the present invention include organic bases which are nontoxic and strong enough to for such salts. These organic bases and the use thereof are readily understood by those skilled in the art. Merely for the purpose of illustration, such organic bases may include mono-, di-, and trialkylamines, such as methylamine, diethylamine and triethylamine; mono-, di-, or trihydroxyalkylamines such as mono-, di-, and triethanolamine; amino acids such as arginine, and lysine; guanidine; N-methylglucosamine; N-methylgioucamine; L-glutamine; N-methylpiperazine; morpho-line; ethylenedianane: N-benzylphenethylamine; tris(hydroxymethyl)antinoethane; and the like.

The acid addition salts of the basic compounds may be prepared by dissolving the free base of the compound of the present invention in aqueous or aqueous alcohol solution or other suitable solvents containing the appropriate acid or base and isolating the salt by evaporating the solution, or by reacting the free base of the compound of the present invention with an acid as well as reacting the compound of the present invention having an acid group thereon with a base such that the reactions are in an organic solvent, in which case the salt separates directly or can be obtained by concentration of the solution.

The compounds of the invention exhibit pharmacological activity and a, therefore, useful as pharmaceuticals. Additionally, the compounds exhibit central nervous and cardiac vesicular system activity.

PARP Assays

1. $IC_{50}$

A convenient method to determine $IC_{50}$ of a PARP inhibitor compound is a PARP assay using purified recombinant human PARP from Trevigan Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 0.1 mg/ml of DNase I activated herring sperm DNA (Sigma, Mo.), 3.0 micromolar [3H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes of incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting.

The compounds of this invention were found to have potent enzymatic activity in the range of a few nM to 20 μM $IC_{50}$ in this inhibition assay.

Using the PARP assays described above, approximate $IC_{50}$ values were obtained for the following compounds:

TABLE I

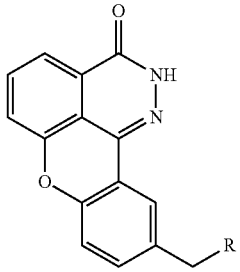

| R = | compound | $IC_{50}$ (uM) |
|---|---|---|
| 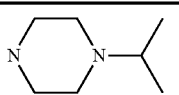 | 4a | 0.03 |
| 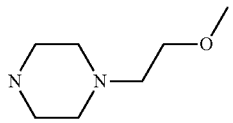 | 4b | 0.02 |
| 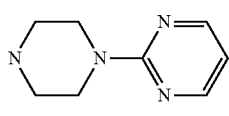 | 4c | 0.03 |
| 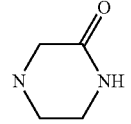 | 4d | 0.02 |
| 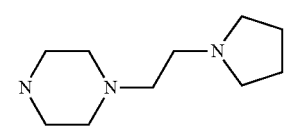 | 4f | N/A |
| 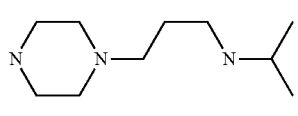 | 4e | N/A |
| 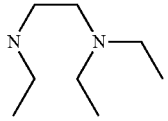 | 4g | 0.5 |
| 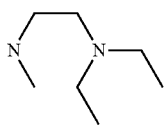 | 4h | 0.1 |
| 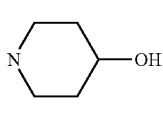 | 4i | 0.04 |
| 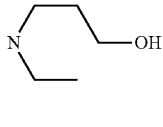 | 4j | 0.1 |

TABLE I-continued

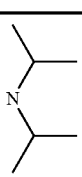

| R = | compound | IC$_{50}$ (uM) |
|---|---|---|
| 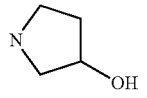 | 4k | 0.3 |
| 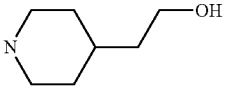 | 4l | 0.1 |
| 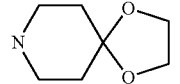 | 4m | 0.1 |
|  | 4n | 0.1 |
| 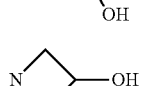 | 4o | 0.05 |
| 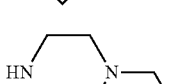 | 4p | 0.03 |
| 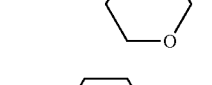 | 4q | 0.05 |
| 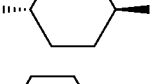 | 4r | 0.03 |
|  | 4s | 0.12 |

2. Measuring Altered Gene Expression in mRNA Senescent Cells

Gene expression alteration may be measured with human fibroblast BJ cells which, at Population Doubling (PDL) 94, are plated in regular growth medium and then changed to low serum medium to reflect physiological conditions described in Linskens, et al., *Nucleic Acids Res.*, 23, 3244-3251 (1995). A medium of DMEM/199 supplemented with 0.5% bovine calf serum is used. The cells are treated daily for 13 days. The control cells are treated with and without the solvent used to administer the PARP inhibitor. The untreated old and young control cells are tested for comparison. RNA is prepared from the treated and control cells according, to the techniques described in PCI Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin West, Arch. perm, 130, 87-95 (1994). Elastin expression of the cells treated with the PARP inhibitor is expected to be significantly increased in comparison with the control cells. Elastin expression should be significantly higher in young cells compared to senescent cells, and thus treatment with the PARP inhibitor should cause elastin expression levels m senescent cells to change to levels similar to those found in much younger cells. Similarly, a beneficial effect should be seen in collagenase and collagen expression with treatment with the PARP inhibitors.

3. Measuring Altered Gene Expression of Protein in Senescent Cells

Gene expression alteration may be measured with approximately 105 BJ cells, at PDL 95-100 which are plated and grown in 15 cm dishes. The growth medium is DMEM/199 supplemented with 10% bovice calf serum. The cells are treated daily for 24 hours with the PARP inhibitors of (100 μg/1 mL of medium). See WO 99/11645. The cells are washed with phosphate buffered solution (PBS), then permeabalized with 4% paraformaldehyde for 5 minutes, then washed with PBS, and treated with 100% cold methanol for 10 minutes, The methanol is removed and the cells are washed with PBS, and then treated with 10% serum to block nonspecific antibody binding. About 1 mL of the appropriate commercially available antibody solutions (1:500 dilution, Vector) is added to the cells and the mixture incubated for 1 hour. The cells are rinsed and washed three times with PBS. A secondary antibody, goat anti-mouse IgG (1 mL) with a biotin tae is added along with 1 mL of is solution containing streptavidin conjugated to alkaline phosphatase and 1 mL of NBT reagent (Vector). The cells are washed and changes in gene expression are noted colorimetrically. Four senescence-specific genes—collagen I, collagen III, collagenase, and interferon gamma—in senescent cells treated with the PARP inhibitor are monitored and the results should show a decrease in interferon gamma expression with no observable change in the expression levels of the other three genes, demonstrating that the PARP inhibitors can alter senescence-specific gene expression.

4. Extending or Increasing Proliferative Capacity and Lifespan of Cells

To demonstrate the effectiveness of the present method for extending the proliferative capacity and lifespan of cells, human fibroblast cells lines (either W138 at Population Doubling (PDL) 23 or BJ cells at PDL 71) are thawed and plated on T75 flasks and allowed to grow in normal medium (DMEM/M199 plus 10% bovine calf serum) for about a week, at which time the cells are confluent, and the cultures are therefor ready to be subdivided. At the time of subdivision, the media is aspirated, and the cells rinsed with phosphate buffer saline (PBS) and then trypsinized. The cells are counted with a Coulter counter and plated at a density of $10^5$ cells per cm$^2$ in 6-well tissue culture plates in DMEM/199 medium supplemented with 10% bovine calf serum and varying amounts (0.10 μM, and 1 mM: from a 100× stock solution in DMEM/M199 medium) of a PARP inhibitor. This process is repeated every 7 days until the cells appear to stop dividing.

The untreated (control) cells reach senescence and stop dividing after about 40 days in culture.

Administration with Temozolomide

Example 1

Oral Administration of Compound 4i + Temozolomide Enhances Survival of Mice Bearing Malignancies at the CNS Site The intracranial transplantation procedure was performed as described in Tentori L et al., "Effect; of single or split exposure of leukemic cells to temozolmnide, combined with poly(ADP-ribose) polymerase inhibitors on cell growth, chromosomal aberrations and base excision repair components," *Cancer Chemother Pharmacol.*, 47, 361-9 (2001). Murine melanoma B16 cells ($10^4$) were injected intracranially (ic) into male B6D2F1 (C57BL/6×DBA/2) mice, Histological evaluation of tumor growth in the brain was performed 1-5 days after tumor challenge, in order to determine the timing of treatment.

Compound 4i was dissolved in 70 mM PBS without potassium and administered pa 1 h before temozolomide (TMZ). TMZ was dissolved in dimethyl-sulfoxide (40 mg/ml), diluted in saline (5 mg/ml) and administered ip at a dose of 100 mg/Kg for five days. Mice were treated with compound 4i by oral gavages once a day for five days, at doses of 10 or 40 mg/kg/day. Median survival times (MST) were determined and the percentage of increase in lifespan (ILS) was calculated as; {[MST (days) of treated mice/MST (days) of control mice]−1}×100. Efficacy of treatments was evaluated by comparing survival curves between treated and control groups.

In mice bearing B16 melanoma, the results indicated that the mean survival time of the groups treated with compound 4i+TMZ combination was significantly higher than that observed in animals receiving TMZ as single agent (Figure I and Table II).

TABLE II

Survival rate of mice bearing B16 melanoma in brain

| Treatment | MST (day) | ILS vs TMZ | P vs TMZ |
|---|---|---|---|
| Control | 14 | | |
| TMZ 100 mg/kg/ip × 5 | 14 | | |
| Compound 4i po (10 mg/kg) + TMZ × 5 | 17 | 21 | 0.001 |
| Compound 4i po (40 mg/kg) + TMZ × 5 | 21 | 50 | <0.0001 |

Example 2

Administration of Compound 4i Enhances the Effect of Temozolomide in a Subcutaneous Melanoma Cancer Model.

The efficacy of TMZ± Compound 4i treatment was also evaluated, on melanoma growing subcutaneously (s.c.) in mice. For this purpose B16 cells ($2.5 \times 10^5$) were inoculated s.c. in the flank of the animal. Tumors were measured with calipers and volume calculated according to the formula: $[(width)^2 \times length]/2$. Drug treatment started 6 days after challenge, when the volume of tumor nodules reached 100-150 mm$^3$. Compound 4i (40 mg/kg po) was administered at 20 rain before temozolomide (100 mg/kg ip) once a day thr five days. Melanoma growth was monitored by measuring tumor nodules every 3 days for 3 weeks.

The combination treatment of Compound 4i+TMZ significantly reduced the growth of B16 melanoma (P<0.01 from day 9 to day 23, vs TMZ alone) (FIG. II).

Example 3

Sympathetic Nerve Conductance Velocity (SNCV) in Cisplatin-induced Neuropathy in Rats The neuroprotective effects of the compounds of the invention were demonstrated in a model of cisplatin-induced neuropathy in rats. Nerve conduction velocity changes are well documented to be a sensitive measure of chemotoxin-induced peripheral neuropathy. Compound 4i was shown to attenuate the deficits in nerve conduction velocity induced by chronic treatment with cisplatin.

In this experiment, female Wistar Hannover rats were dosed with neuropathy inducing doses of cisplatin (2 mg/kg IP; twice a week for 4 weeks) with and without compound 4i (40 mg/kg PO daily). The rats were monitored for changes in sensory nerve conduction velocity (SNCV) in the caudal nerve at baseline (pre-cisplatin dosing) and after treatment. Additionally, dorsal root ganglion and sciatic nerve specimens with morphometric analysis on dorsal root ganglion neurons (somatic, nuclear and nucleolar size) were assessed histopathologically.

At the beginning and end of the treatment period each animal underwent the determination of SNCV in the tail as previously described in Cavaletti et al., "Protective Effects of glutathione on cisplatin neurotoxicity in rats," *Int. J. Radiation Oncology,* 29, 771-776 (1994) and Tredici et al., "Low-Dose Glutathione Administration in the prevention of cisplatin-induced peripheral neuropathy in rats," *Neuro toxicology,* 15, 701-704 (1994.) The antidromic SNCV in the tail nerve was assessed by placing recording ring electrodes distally in the tall, while the stimulating ring electrodes were placed 5 cm and 10 era proximally with respect to the recording point. The latencies of the potentials recorded at the 2 sites after nerve stimulation were determined (peak-to-peak) and nerve conduction velocity was calculated accordingly.

Left L5 dorsal root ganglia (DRG) of rats from each group were obtained from the sacrificed animals and processed according to previously reported protocols [Cavaletti et al.; Tredici et al], resin embedded, and used for light and electron microscope observations and morphometry. On 1 μm thick semithin sections, morphometric determinations of the cross sectional area of the somata, nuclei and nucleoli of DRG neurons were performed using an image analysis software (Image J, NIH).

The differences in nerve conduction velocity, and in morphometric data obtained in dorsal root ganglia neurons during the experiment were statistically evaluated using the analysis of variance (ANOVA) and the Tukey-Kramer post-test (significance level set at p<0.05).

The co-administration of compound 4i was found to induce a statistically significant reduction in the tail nerve conduction velocity impairment due to chronic cisplatin treatment (Tables 3 and 4).

TABLE 3

| SNCV at the end of the experiment (m/sec) | | | |
|---|---|---|---|
| | controls | CDDP | CDDP + 4i |
| Number of values | 6 | 8 | 8 |
| Mean (m/sec) | 41.73 | 28.62 | 34.08 |
| Std. Deviation | 1.718 | 0.5194 | 0.6128 |
| Std. Error | 0.7014 | 0.1836 | 0.2166 |

CDDP = Cisplatin

TABLE 4

| Statistical analysis (one-way ANOVA) | | | | |
|---|---|---|---|---|
| Tukey's Multiple Comparison Test | Mean Diff. | q | P value | 95% CI of diff |
| CDDP vs CDDP + 4i | −5.460 | 14.90 | P < 0.001 | −7.016 to −3.905 |

DRG Morphometry.

A Morphometric study on DRG neurons revealed a significant effect only on the somatic size of DRG neurons with compound 4i. Table 5 shows morphometry results, and statistical data is listed in Tables 6 (soma), and 7 (nucleolus).

TABLE 5

| Morphometry on DRG ($\mu m^2$) | | | | | | |
|---|---|---|---|---|---|---|
| | Soma controls | Nu controls | Nucl controls | Soma CDDP | Nu CDDP | Nucl CDDP |
| Mean | 878.3 | 122.0 | 9.196 | 683.4 | 114.3 | 7.651 |
| Std. Deviation | 547.1 | 56.46 | 5.997 | 376.7 | 50.05 | 4.268 |
| Std. Error | 23.48 | 2.423 | 0.2573 | 15.89 | 2.111 | 0.1800 |
| | Soma CDDP + 4i | | Nu CDDP + 4i | | Nucl CDDP + 4i | |
| Mean | 822.1 | | 121.8 | | 8.069 | |
| Std. Deviation | 498.2 | | 55.25 | | 4.587 | |
| Std. Error | 20.60 | | 2.284 | | 0.1897 | |

Nu = nucleus,
Nucl = nucleolus

TABLE 6

| Soma | | | | |
|---|---|---|---|---|
| Tukey's Multiple Comparison Test | Mean Diff. | q | P value | 95% CI of diff |
| CDDP vs CDDP + 4i | −138.7 | 7.136 | P < 0.001 | −213.7 to −63.57 |

TABLE 7

| Nucleolus | | | | |
|---|---|---|---|---|
| Tukey's Multiple Comparison Test | Mean Diff. | q | P value | 95% CI of diff |
| CDDP vs CDDP + 4i | −0.4177 | 2.023 | P > 0.05 | −1.215 to 0.3799 |

The invention being thus described, it will be obvious that the same may be varied in many ways. Such variations are not to be regarded as a departure from the spirit and scope of the invention, and all such modifications are intended to be included within the scope of the following claims.

INCORPORATION BY REFERENCE

All publications, patents, and pre-grant patent application publications cited in this specification are herein incorporated by reference, and for any and all purposes, as if each individual publication or patent application were specifically and individually indicated to be incorporated by reference. In the case of inconsistencies the present disclosure will prevail.

We Claim:

1. A compound:

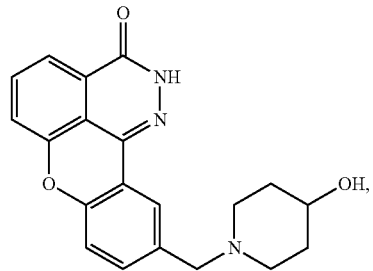

and pharmaceutically acceptable salts, esters, and mixtures thereof.

2. The compound of claim 1:

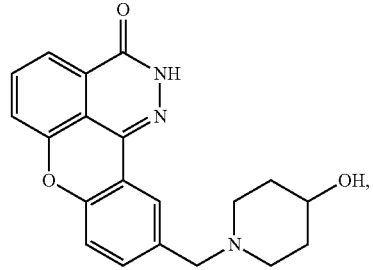

and pharmaceutically acceptable salts thereof.

3. The compound of claim 1:

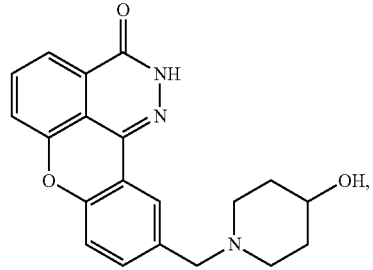

and esters thereof.

4. A pharmaceutical composition comprising a therapeutically effective amount of a compound:

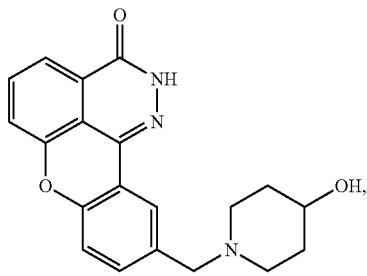

and pharmaceutically acceptable salts, esters, and mixtures thereof; and a pharmaceutically acceptable carrier, diluent, or excipient.

5. The pharmaceutical composition of claim 4, wherein said compound is

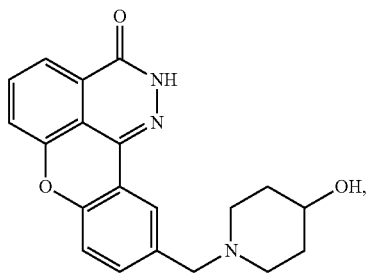

and pharmaceutically acceptable salts thereof.

6. The pharmaceutical composition of claim 4, wherein said compound is

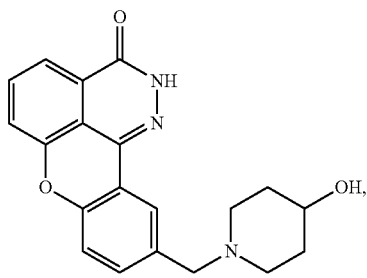

and esters thereof.

7. The pharmaceutical composition of claim 5, further comprising a chemotherapeutically effective amount of at least one chemotherapeutic agent, wherein the chemotherapeutic agent is selected from a taxoid, temozolomide, dactinomycin, danorubicin, doxorubicin, 4'-deoxydoxorubicin, bleomycin, pilcamycin, mitomycin, neomycin and gentamycin, etoposide, 4-OH cyclophosphamide, a platinum coordination complex, and mixtures thereof.

8. The pharmaceutical composition of claim 7 wherein said chemotherapeutic agent is temozolomide.

9. A method of treating diseases or conditions selected from the group consisting of neural tissue damage resulting from ischemia and reperfusion injury, depression, inflammatory bowel disorders, gout, chronic pain, acute pain, neuropathic pain, renal failure, retinal ischemia, and septic shock, in an animal comprising administering to said animal an effective amount of a compound:

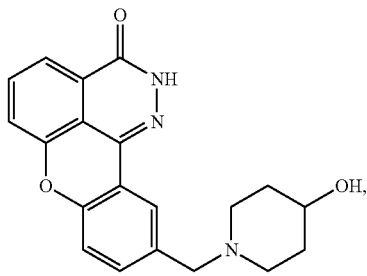

and pharmaceutically acceptable salts, esters, and mixtures thereof.

10. The method of claim 9, wherein said compound is

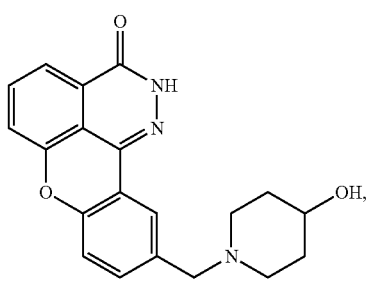

and pharmaceutically acceptable salts thereof.

11. The method of claim 9, wherein said compound is

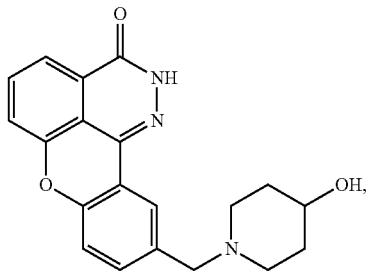

and esters thereof.

12. The method of claim 10, wherein said ischemia or reperfusion injury is cerebral injury after cardiac arrest and cardio-pulmonary resuscitation.

13. The method of claim 10, wherein septic shock is endotoxic shock.

14. The method of claim 10, wherein the inflammatory bowel disorder is colitis.

15. The method of claim 10, wherein the inflammatory bowel disorder is Crohn's disease.

16. A method of radiosensitizing tumor cells in a mammal in need of radiation therapy, comprising: administering to said mammal a compound:

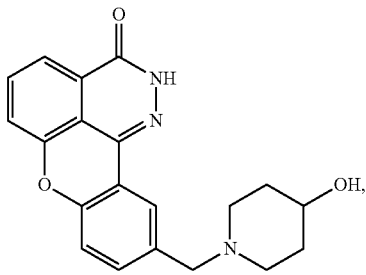

and pharmaceutically acceptable salts, esters, and mixtures thereof; in an amount sufficient to sensitize said tumor cells to the effects of said radiation therapy.

17. The method of claim 16, wherein said compound is

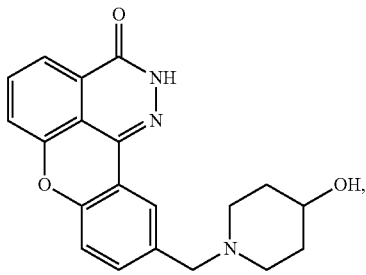

and pharmaceutically acceptable salts thereof.

18. The method of claim 16, wherein said compound is

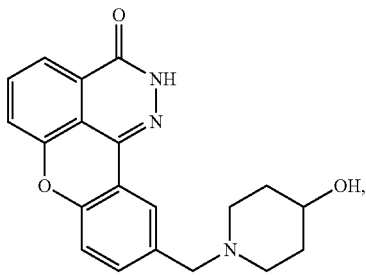

and esters thereof.

19. The method of claim 17 wherein the tumor cells are selected from the group consisting of ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostrate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

20. The method of claim 17 wherein the mammal is human.

21. A method of therapy comprising: chemosensitizing tumor cells in a mammal in need of chemotherapy by administering to said mammal a compound:

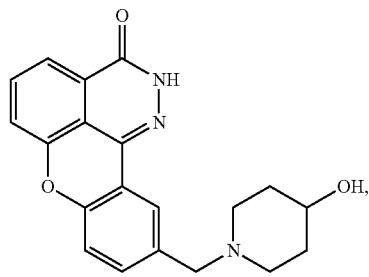

and pharmaceutically acceptable salts, esters, and mixtures thereof; in an amount sufficient to sensitize said tumor cells to the effects of at least one chemotherapeutic agent.

22. The method of claim 21, wherein said compound is

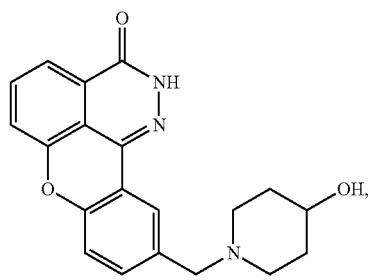

and pharmaceutically acceptable salts thereof.

23. The method of claim 21, wherein said compound is

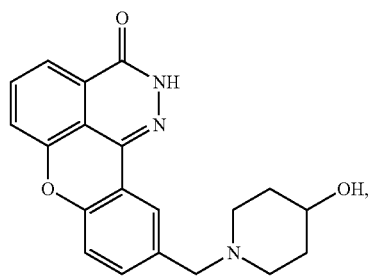

and esters thereof.

24. The method of claim 22, wherein said mammal is a human.

25. The method of claim 22, further comprising, first: allowing a time period following administration of said compound to provide an effective amount of chemosensitization, and, second: administering to said mammal a pharmaceutically-effective dose of said chemotherapeutic agent.

26. The method of claim 22, wherein said compound is administered in a pharmaceutical composition comprising said compound and a pharmaceutically acceptable carrier, diluent, or excipient.

27. The method of claim 22, further comprising administering to said mammal a therapeutically-effective dose of said chemotherapeutic agent, wherein said chemosensitizing compound and said chemotherapeutic agent are administered essentially simultaneously.

28. The method of claim 22, wherein said chemotherapeutic agent is selected from the group consisting of taxoid, temozolomide, adriamycin, camptothecin, carboplatin, cisplatin, daunorubicin, docetaxel, doxorubicin, interferon (alpha, beta, gamma), interleukin 2, irinotecan, paclitaxel, topotecan, therapeutically effective analogs and derivatives of the same, and mixtures thereof.

29. The method of claim 22, wherein said chemotherapeutic agent is temozolomide.

30. The method of claim 23, wherein said chemotherapeutic agent is selected from the group consisting of taxoid, temozolomide, adriamycin, camptothecin, carboplatin, cisplatin, daunorubicin, docetaxel, doxorubicin, interferon (alpha, beta, gamma), interleukin 2, irinotecan, paclitaxel, topotecan, therapeutically effective analogs and derivatives of the same, and mixtures thereof.

31. The method of claim 23, wherein said chemotherapeutic agent is temozolomide.

* * * * *

UNITED STATES PATENT AND TRADEMARK OFFICE
CERTIFICATE OF CORRECTION

Page 1 of 1

PATENT NO. : 8,058,275 B2
APPLICATION NO. : 12/910448
DATED : November 15, 2011
INVENTOR(S) : Weizheng Xu et al.

It is certified that error appears in the above-identified patent and that said Letters Patent is hereby corrected as shown below:

Column 45, lines 65-66, delete "prostrate cancer" and insert --prostate cancer--.

Signed and Sealed this
Thirty-first Day of January, 2012

David J. Kappos
*Director of the United States Patent and Trademark Office*